United States Patent
Fukazawa

(10) Patent No.: US 10,523,874 B2
(45) Date of Patent: Dec. 31, 2019

(54) IMAGE PROCESSING APPARATUS, IMAGE PROCESSING METHOD, AND PROGRAM

(71) Applicant: SONY CORPORATION, Tokyo (JP)

(72) Inventor: Kentaro Fukazawa, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/060,282

(22) PCT Filed: Dec. 21, 2016

(86) PCT No.: PCT/JP2016/088251
§ 371 (c)(1),
(2) Date: Jun. 7, 2018

(87) PCT Pub. No.: WO2017/141544
PCT Pub. Date: Aug. 24, 2017

(65) Prior Publication Data
US 2018/0367721 A1 Dec. 20, 2018

(30) Foreign Application Priority Data
Feb. 16, 2016 (JP) ................................. 2016-026771

(51) Int. Cl.
*H04N 5/235* (2006.01)
*H04N 5/232* (2006.01)

(52) U.S. Cl.
CPC ......... *H04N 5/2352* (2013.01); *H04N 5/2355* (2013.01); *H04N 5/23296* (2013.01); *H04N 5/2351* (2013.01)

(58) Field of Classification Search
None
See application file for complete search history.

(56) References Cited

U.S. PATENT DOCUMENTS 9,711,553 B2 * 7/2017 Kim .................. H01L 27/14609
2010/0277634 A1 * 11/2010 Watanabe .......... H04N 5/23212
348/311

(Continued)

FOREIGN PATENT DOCUMENTS

JP 2003-9006 A 1/2003
JP 2013-162347 A 8/2013

(Continued)

OTHER PUBLICATIONS

International Search Report dated Feb. 26, 2017, in PCT/JP2016/088251 filed Dec. 21, 2016.

*Primary Examiner* — Cynthia Segura
(74) *Attorney, Agent, or Firm* — Xsensus, LLP

(57) ABSTRACT

[Object] To improve an sn ratio and to make the image quality good in addition to the expanding of the dynamic range of an image.
[Solution] An image processing apparatus according to the present disclosure includes: a light amount determining section that determines, on a basis of a pixel value of each pixel of an imaged image, on a basis of a pixel value of each pixel of an imaged image, a light amount of the imaged image; and an exposure ratio determining section that determines a ratio of an exposure amount of a long time exposure pixel to an exposure amount of a short time exposure pixel on a basis of a ratio of pixels the pixel value of each of which is saturated, among pixels included in a region of the imaged image.

19 Claims, 19 Drawing Sheets

(56) References Cited

U.S. PATENT DOCUMENTS

| | | | |
|---|---|---|---|
| 2013/0050529 A1* | 2/2013 | Murayama | H04N 5/3572 348/234 |
| 2013/0135492 A1* | 5/2013 | Ikeda | H04N 5/225 348/222.1 |
| 2014/0205193 A1* | 7/2014 | Umezu | H04N 5/2355 382/169 |
| 2014/0375815 A1* | 12/2014 | Kanou | H04N 5/2351 348/148 |
| 2015/0244916 A1* | 8/2015 | Kang | H04N 5/2355 348/222.1 |
| 2015/0244923 A1* | 8/2015 | Lee | H04N 9/045 348/234 |
| 2017/0013181 A1* | 1/2017 | Marcelpoil | G01N 21/255 |
| 2017/0048443 A1* | 2/2017 | Tokui | H04N 5/23216 |
| 2017/0095297 A1* | 4/2017 | Richmond | A61B 1/00006 |
| 2017/0264831 A1* | 9/2017 | Hyuga | H04N 5/2353 |
| 2018/0080877 A1* | 3/2018 | Hirawake | G01N 21/6456 |
| 2018/0343390 A1* | 11/2018 | Duran | H04N 5/23245 |

FOREIGN PATENT DOCUMENTS

| | | |
|---|---|---|
| JP | 2014-39170 A | 2/2014 |
| JP | 2014-230708 A | 12/2014 |
| JP | 2015-213276 A | 11/2015 |

* cited by examiner

FIG. 17
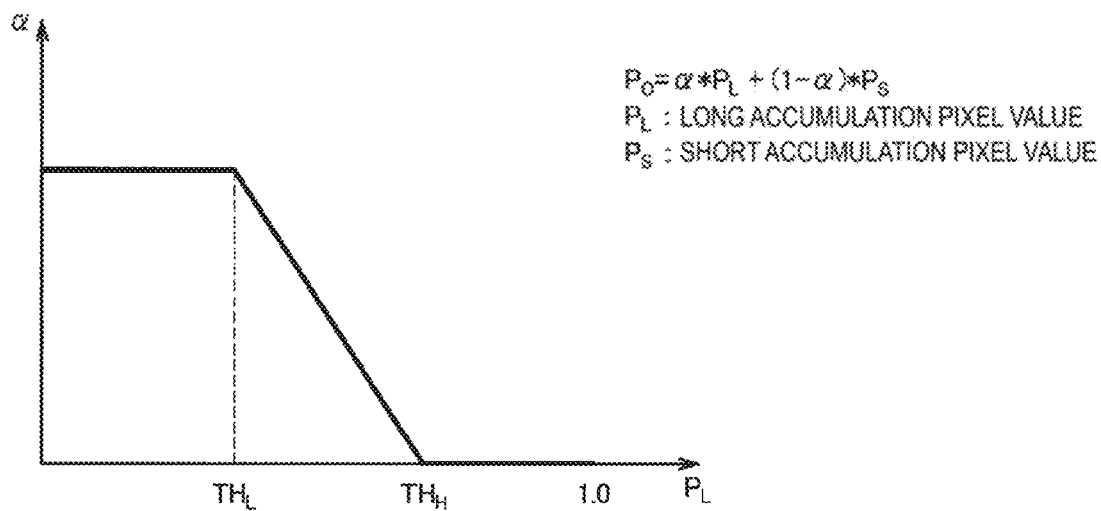
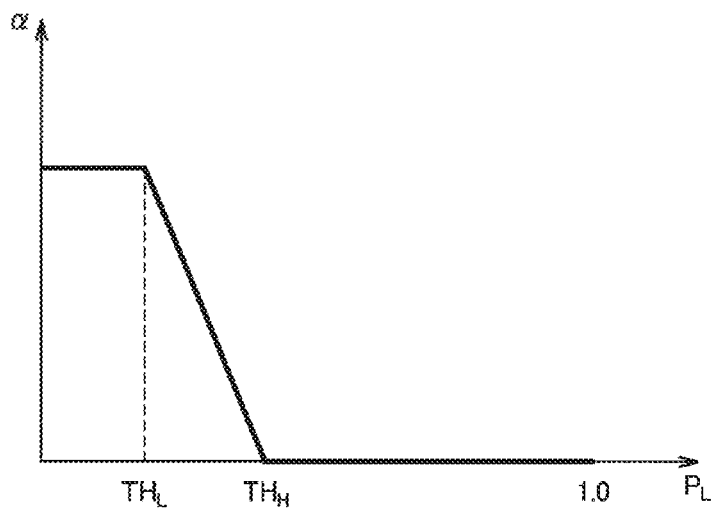

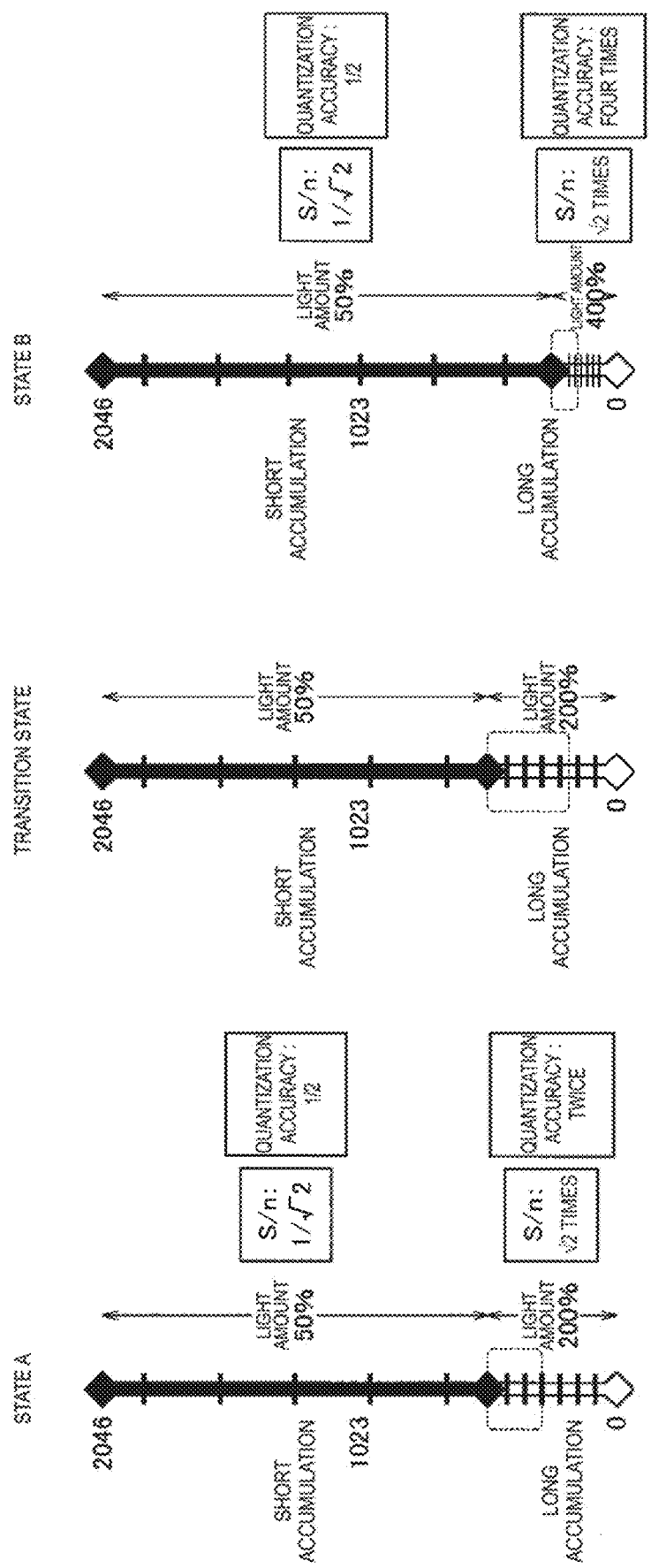

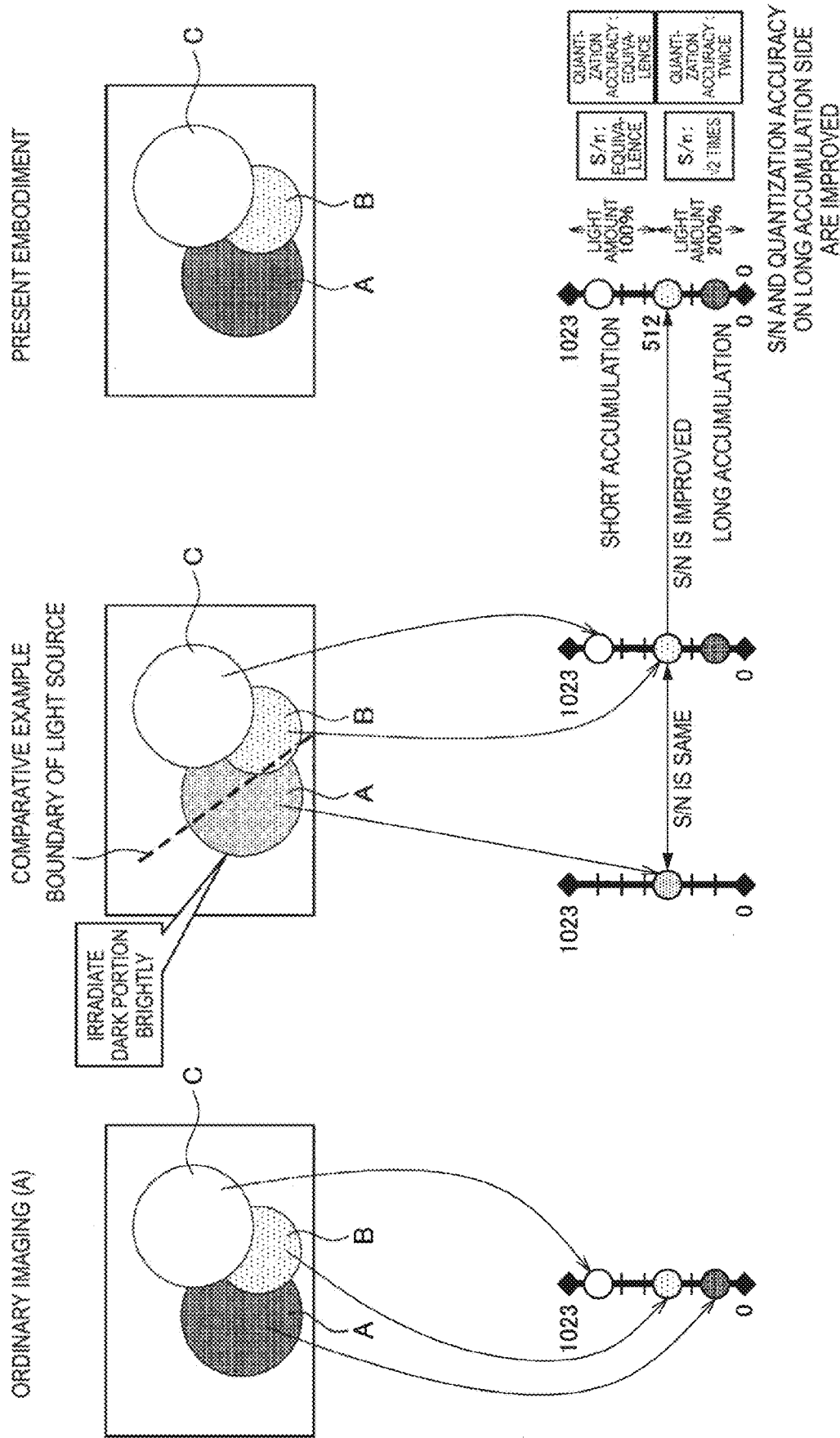

IMAGE PROCESSING APPARATUS, IMAGE PROCESSING METHOD, AND PROGRAM

TECHNICAL FIELD

This disclosure relates to an image processing system, an image processing method, and a program.

BACKGROUND ART

Hitherto, for example, in an endoscope that is inserted in an inside of an observation target and images while irradiating an object in the inside of the observation target, the below-described Patent Literature 1 describes a technique to perform light distribution control for changing a peak position in a synthesized light distribution by adjusting the projected light intensity of each of a first lighting section and to second lighting section.

CITATION LIST

Patent Literature

Patent Literature 1: JP 2014-230708A

DISCLOSURE OF INVENTION

Technical Problem

However, in the technique described in the above-described patent literature, since a region where a light amount is not increased by the lighting section occurs especially on a low luminance portion, there is a problem that an sn ratio and quantization accuracy cannot be improved.

Moreover, in the technique described in the above-described patent literature 1, since a plurality of light source light amounts is controlled for each region, in the case where the boundary between a dark, region and a light region does not coincide the boundary of the light sources, there is a problem that the lightness of an object at the time of imaging becomes uneven, and the image quality lowers.

Then, it has been required to improve an sn ratio and to make the image quality good in addition to the expanding of the dynamic range of an image.

Solution to Problem

According, to the present disclosure, there is provided an image processing apparatus including: a light amount determining section that determines, on a basis of a pixel value of each pixel of an imaged image, a light amount of the imaged image; and an exposure ratio determining section that determines a ratio of an exposure amount of a long time exposure pixel to an exposure amount of a short time exposure pixel on a basis of a ratio of pixels the pixel value of each of which is saturated, among pixels included in a region of the imaged image.

In addition, according to the present disclosure, there is provided an image processing method including: determining, on a basis of a pixel value of each pixel of an imaged image, a light amount of the imaged image; and determining a ratio of an exposure amount of a long time exposure pixel to an exposure amount of a short time exposure pixel on a bask of a ratio of pixels the pixel value of each of which is saturated, among pixels included in a region of the imaged image.

In addition, according to the present disclosure, there is provided a program for causing a computer function as: means for determining, on a basis of a pixel value of each pixel of an imaged image, a light amount of the imaged image, and means for determining a ratio of an exposure amount of a long time exposure pixel to an exposure amount of a short time exposure pixel on a basis of a ratio of pixels the pixel value of each of which is saturated, among pixels included in a region of the imaged image.

Advantageous Effects of Invention

As described above, according to this disclosure, while expanding the dynamic range of an image, it becomes possible to improve an sn ratio and to make the image quality good.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 17 is a characteristic diagram showing a situation that the value of a coefficient "a" changes correspondingly to the pixel value $P_L$ of long accumulation pixels.

FIG. 19 is, a schematic diagram showing an example in which a saturation level is not changed in the case of transiting from a state A to a state B by charming an exposure ratio.

FIG. 20 is a schematic diagram showing by comparing ordinary imaging (A), HDR imaging (E) according to the present embodiment, and a comparative example in the case of imaging the same object.

MODE(S) FOR CARRYING OUT THE INVENTION

Figure 1:
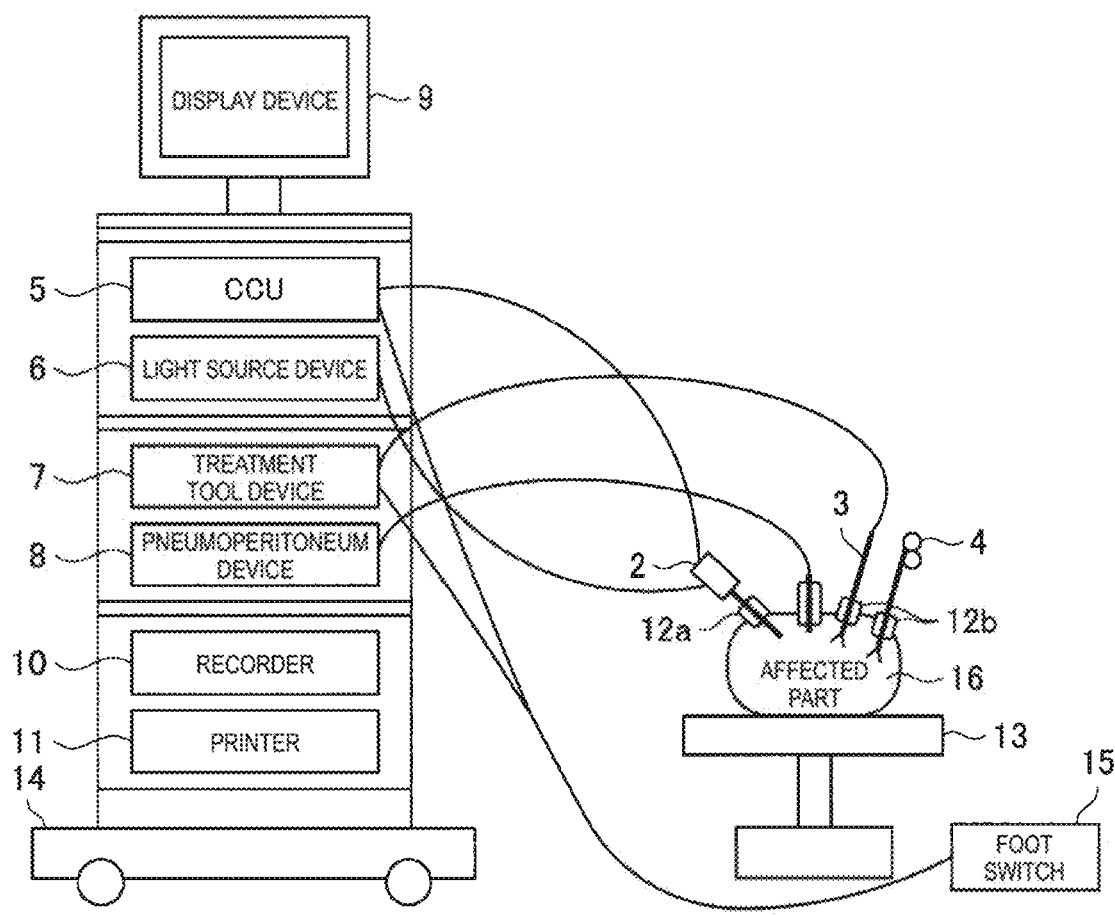
FIG. 1 is a schematic diagram showing a schematic constitution of an endoscope system according to one embodiment of this disclosure.

Hereinafter, (a) preferred embodiment(s) of the present disclosure will described in detail with reference w the appended drawings. Note that, in this specification and the appended drawings, structural elements that have substantially the same function and structure are denoted with the same reference numerals, and repeated explanation of these structural elements is omitted.

It should be noted that description will be given in the following order.
1. Endoscopic system
2. Constitution example of CCU
3. With regard to HDR imaging according to present embodiment
4. With regard to light amount determining process
5. With regard to mode different from present embodiment
6. With regard to mixture of long accumulation pixel and short accumulation pixel
7. Comparison between present embodiment and comparative example 1. Endoscopic System First, with reference to FIG. 1, a schematic constitution of an endoscope system 100 according to one embodiment of the present disclosure will be described. In the health care site, endoscopic surgeries have recently been carried out in the place of conventional abdominal surgeries. For example, in the case where an abdominal surgery is carried out, an endoscopic surgery system 1 which is arranged in a surgery room as shown in FIG. 1 is used. Instead of carrying out a laparotomy by cutting, the abdominal wall as in the past, opening tools called trocars 12a and 12b are attached at several parts of the abdominal wall, and, through a hole provided to each of the trocars 12a and 12b, a laparoscope (hereinafter, may also be referred to as endoscope) 2, an energy treatment tool 3, a pair of forceps 4, and the like are inserted into the body. The endoscope 2 includes a camera head 200 including an image sensor that images an image. Then, while watching on a real-time basis an image of an affected part (tumor or the like) 16, which is captured as video by the endoscope 2, procedures such as resecting the affected part 16 us ng the energy treatment tool 3 are performed. The endoscope 2, the energy treatment tool 3, and the pair of forceps 4 are held by a surgeon, an assistant, a scopist, or a robot, or the like.

Inside the surgery room in which such air endoscopic surgery is carried out, there is provided a cart 14 which is loaded with devices for the endoscopic surgery, a patient's bed 13 on which a patient lies, a foot switch 15, and the like. The cart 14 is loaded with medical devices, such as a camera control unit (CCU) 5, a light source device 6, a treatment tool device 7, a pneumoperitoneum device 8, a display device 9. a recorder 10, and a printer 11.

An image signal of the affected part 16 which is imaged through an observation optical system of the endoscope 2 is transmitted to the CCU 5 via a camera cable, subjected to signal processing in the CCU 5, and then output to the display device 9. Thus, an endoscope image of the affected part 16 is displayed. The CCU 5 may be connected to the endoscope 2 via the camera cable, or may be wirelessly connected to the endoscope 2.

The light source device 6 is connected to the endoscope 2 through a light guide cable, and, can irradiate the affected part 16 by switching over light of various wave lengths.

The treatment tool device 7 is, for example, a high frequency output device that outputs high frequency currents for the energy treatment tool 3 that cuts the affected part 16 using electric heat.

The pneumoperitoneum device 8 includes air supply means and air-suction means, and is a device that supplies the inside of the body of a patient, for example, the abdominal region, with air. The foot switch 15 uses a foot operation of the surgeon, the assistant, or the like as a trigger signal and controls the CCU 5, the treatment tool device 7, and the like.

2. Constitution Example of CCU

Figure 2:
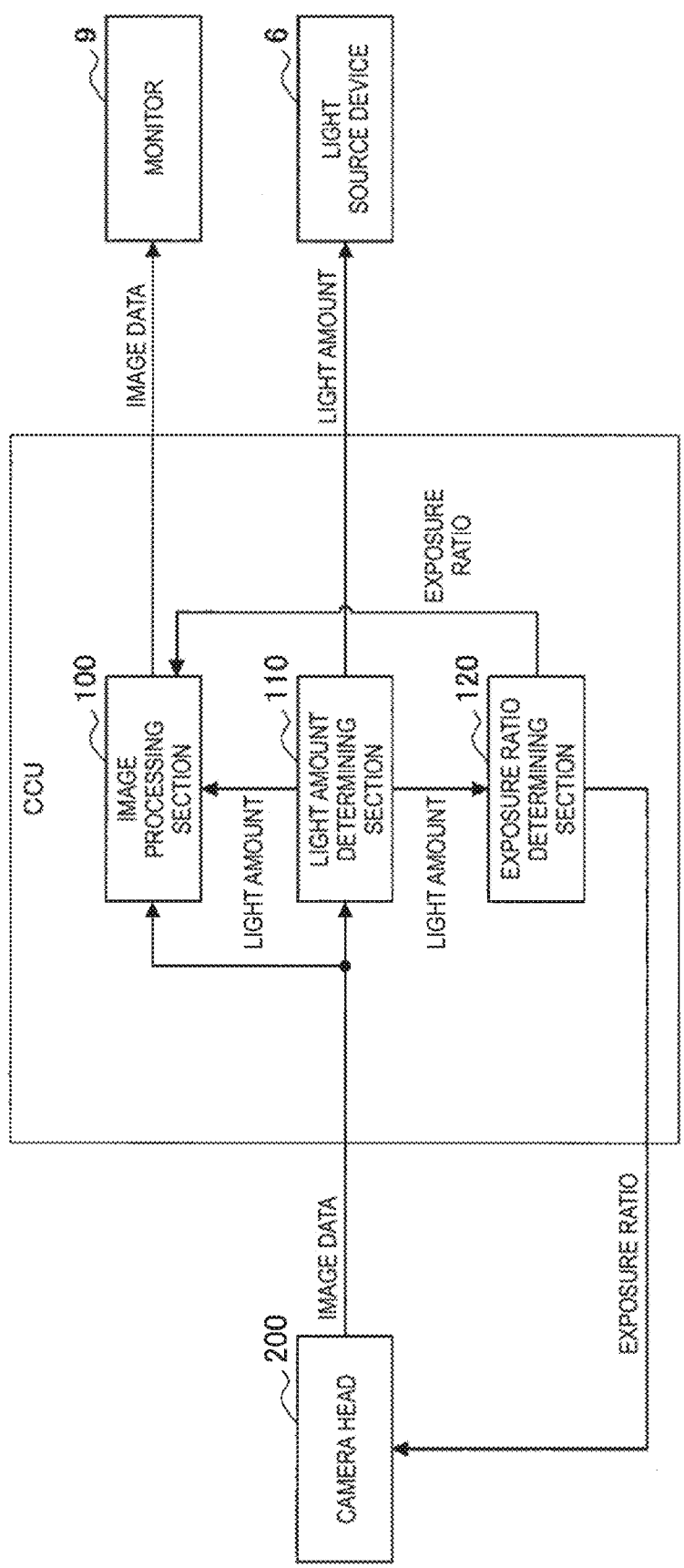
FIG. 2 is a schematic diagram showing a CCU and a constitution in the vicinity of it.

FIG. 2 is a schematic diagram showing a CCU (image processing apparatus) 5 and a constitution in the vicinity of it. The CCU 5 includes an image processing section 100, a light amount determining section 110, and an exposure ratio determining, section 120. To the CCU 5, a camera head 200, the display device (monitor) 9, and the light source device 6 are connected. In the constitution shown in FIG. 2, an incident light amount for an image sensor is controlled with a light amount irradiated to an object from the light source device 6. In this connection, each constitution component of the CCU 5 shown in FIG. 2 can include a central processing unit, such as CPU, and a program (software) to make this function.

The image data (the pixel value of each pixel) of an image of an object imaged by the image sensor of the camera head 200 are sent to the CCU 5. The light amount determining section 110 determines a light amount on the basis of the pixel values, and, sends the light amount the light amount to the light source device 6, The light source device 6 irradiates light to an object on the basis of the received light amount. In this connection, a process in which the light amount determining section 110 determines a light amount will be described later in detail.

The exposure ratio determining section 120 determines an exposure ratio on the basis of pixel values, and, sends the exposure ratio to the camera head 200. Here, the exposure ratio is a ratio of an exposure amount of long accumulation pixels to an exposure amount of short accumulation pixels. The camera head 200 performs imaging by adjusting an exposure time for long accumulation pixels and short accumulation pixels on the basis of an exposure ratio, and, adjusts pixel values. In this connection, a process in which the exposure ratio determining section 120 310 determines a light amount, will be described later in detail.

The image processing section 100 performs various kinds of image processing in order to output an input image from the camera head 200 to the display device 9. Moreover, in the case of having expanded the dynamic range of short accumulation pixels correspondingly to an exposure ratio with a technique mentioned later, the, image processing section 199 adjusts the pixel value of short accumulation pixels correspondingly to an exposure ratio. Moreover, in the case of having increased the light amount of long accumulation pixels, the image processing section 100 adjusts the pixel values of long and short accumulation pixels correspondingly to a light amount. Furthermore, the image processing section 100 performs a process of mixing long accumulation pixels and short accumulation pixels.

The camera head 200 includes an image sensor with which HDR imaging is possible. The HDR imaging is an imaging method of expanding a dynamic range by synthesizing images imaged under a plurality of different exposure conditions. To the camera head 200, an exposure ratio determined by the exposure ratio determining section is sent. The image sensor determines the exposure time of long accumulation pixels and the exposure time of short accumulation pixels on the basis of an exposure ratio, and, performs exposure. Here, the exposure time of short accumulation pixels becomes less than the exposure time of long accumulation pixels correspondingly to an exposure ratio.

3. With Regard to HDR Imaging According to Present Embodiment

Figure 3:
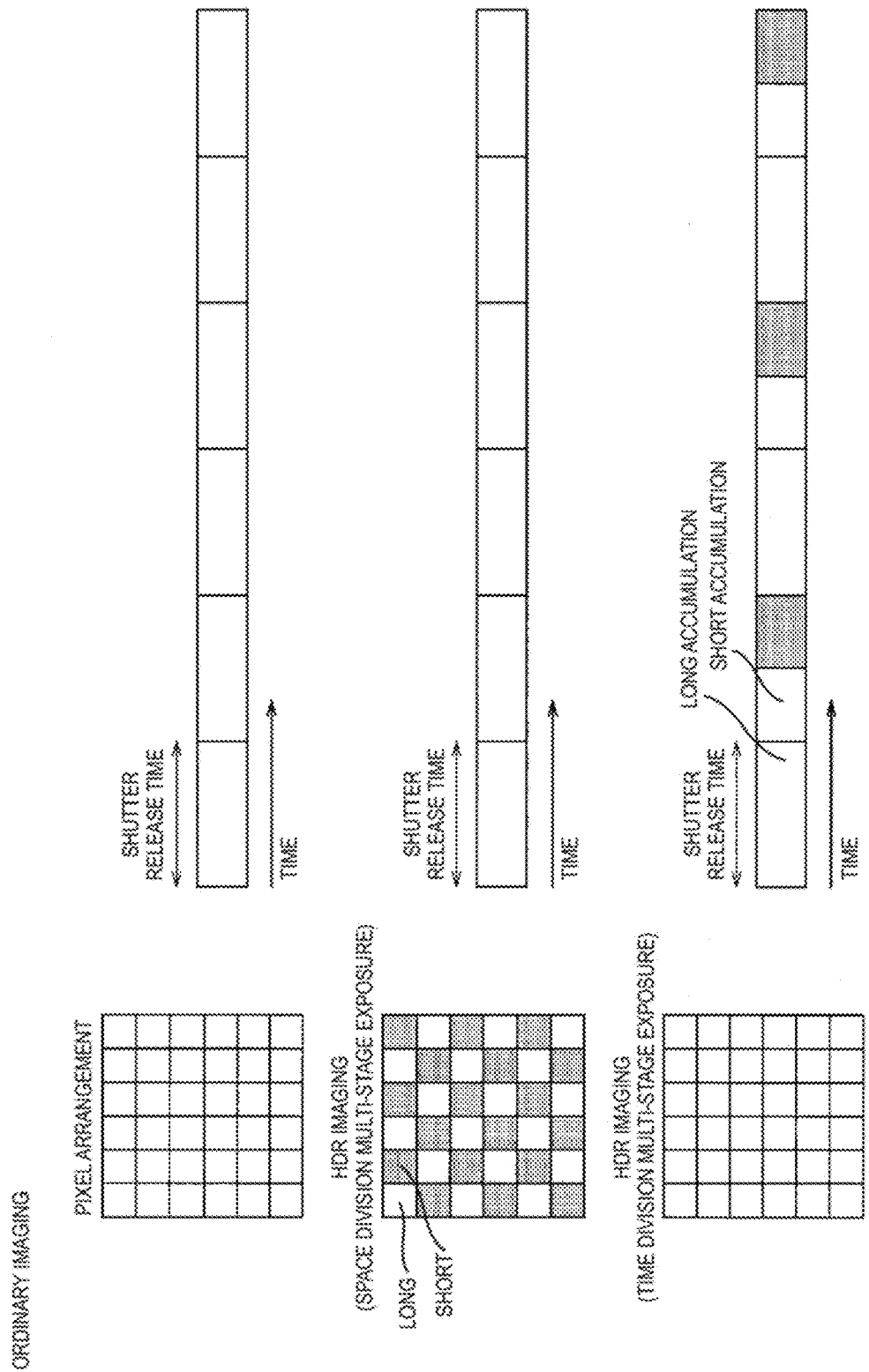
FIG. 3 is a schematic diagram showing by comparing ordinary imaging, HDR imaging (space division multi-stage exposure), and HDR imaging (time division multi-stage exposure).

FIG. 3 is a schematic diagram showing by comparing ordinary imaging, HDR imaging (space division multi-stage exposure), and HDR imaging (time division multi-stage exposure). In the ordinary imaging, an exposure time (shutter release time) of all the pixels is made the same, and exposure is performed for all the pixel with the same exposure time for each frame.

On the other hand, in the HDR imaging (space division multi-stage exposure), long time exposure pixels and short time exposure pixels exist mixedly in a space, and as an example, long time exposure pixels and short time exposure pixels are arranged in a staggered pattern. Here, the long time exposure pixel is, referred to as a long accumulation pixel, and the short time exposure pixel is referred to as a short accumulation pixel. For each frame, in the long accumulation pixel and the short accumulation pixel, exposure is performed for respective different times.

Moreover, in the HDR imaging (time division multi-stage exposure), a long time exposure frame and a short time exposure frame are switched over in a time direction. In addition, as the HDR imaging, a system that divides incident light and images with image sensors different in sensitivity, also may be considered.

Figure 4:
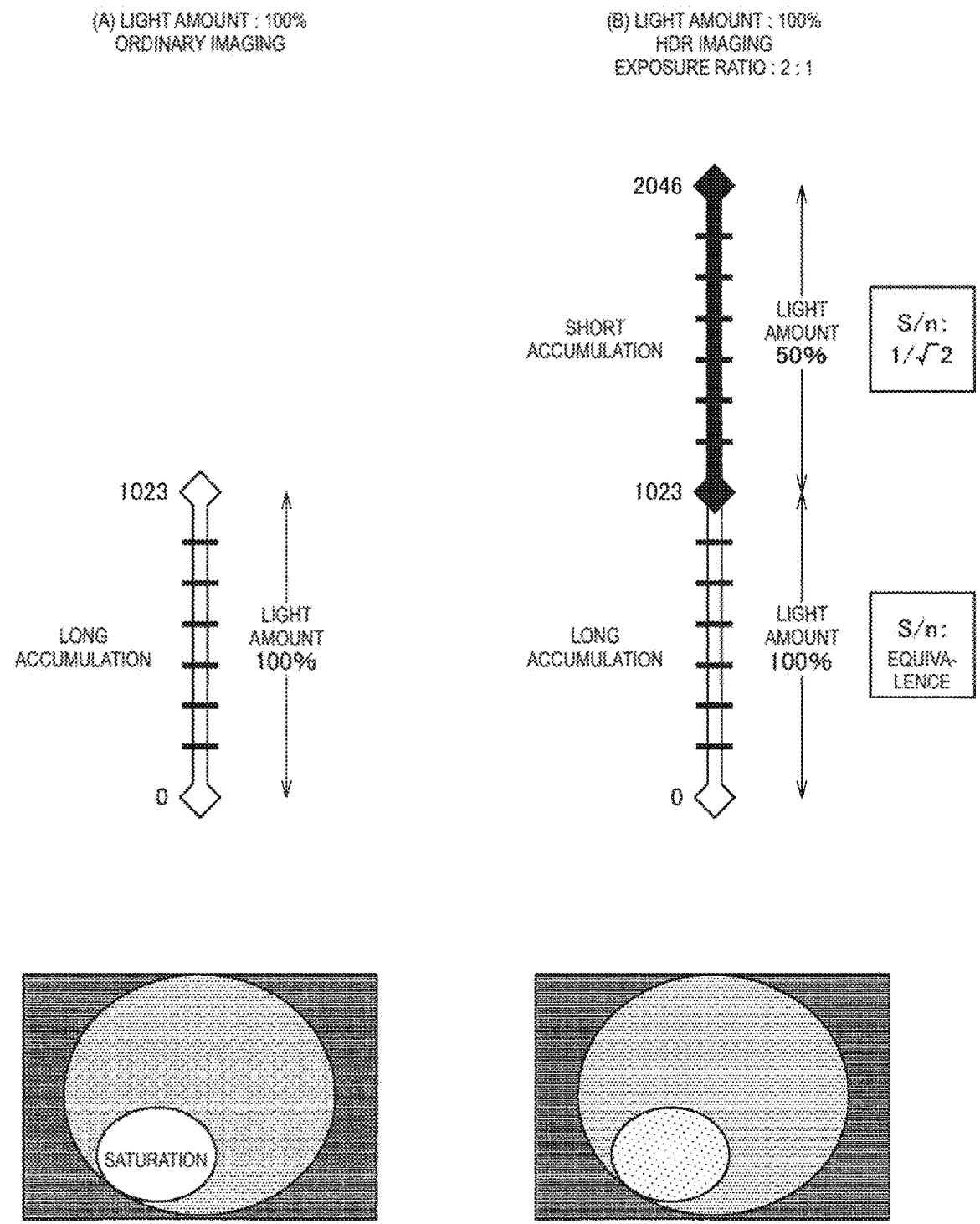
FIG. 4 is a schematic diagram showing a relationship between an exposure ratio and a dynamic range according to the present embodiment.

FIG. 4 is a schematic diagram showing a relationship between an exposure ratio and a dynamic range according to the present embodiment. In the ordinary imaging (A), the light amount of an object is made 100%, and a pixel value is acquired in each pixel by imaging. In the case where the dynamic range of an image sensor is made 10 bits, a pixel value of 0 to 1023 can be acquired. Like an image shown in the lower stage in FIG. 4, a range of a light amount exceeding a pixel value of 1023 in an image becomes a saturated region.

On the other hand, in the HDR imaging (B) according to the present embodiment, for long accumulation pixels, imaging is performed similarly to the ordinary imaging (A), and, for short accumulation pixels, imaging is performed by making the light amount of an object 50%. Then, for the short accumulation pixels, the image processing section 100 doubles the pixel value acquired by the imaging. With this, in the short accumulation pixels, a pixel value of 0 to 2046 can be acquired, whereby a dynamic range can be expanded, and, since a saturation level becomes twice relative to the ordinary imaging (A), a saturated region in an image can be decreased. In an image shown in the lower stage in FIG. 4, a saturated region is decreased in the HDR imaging (B) relative to the ordinary imaging (A). In the short accumulation pixels, since the light amount is 50%, an sn ratio (s/n) becomes 1/√2 relative to the ordinary imaging. On the other hand, the s/n of the long accumulation pixels is the same as that in the ordinary imaging.

Figure 5:
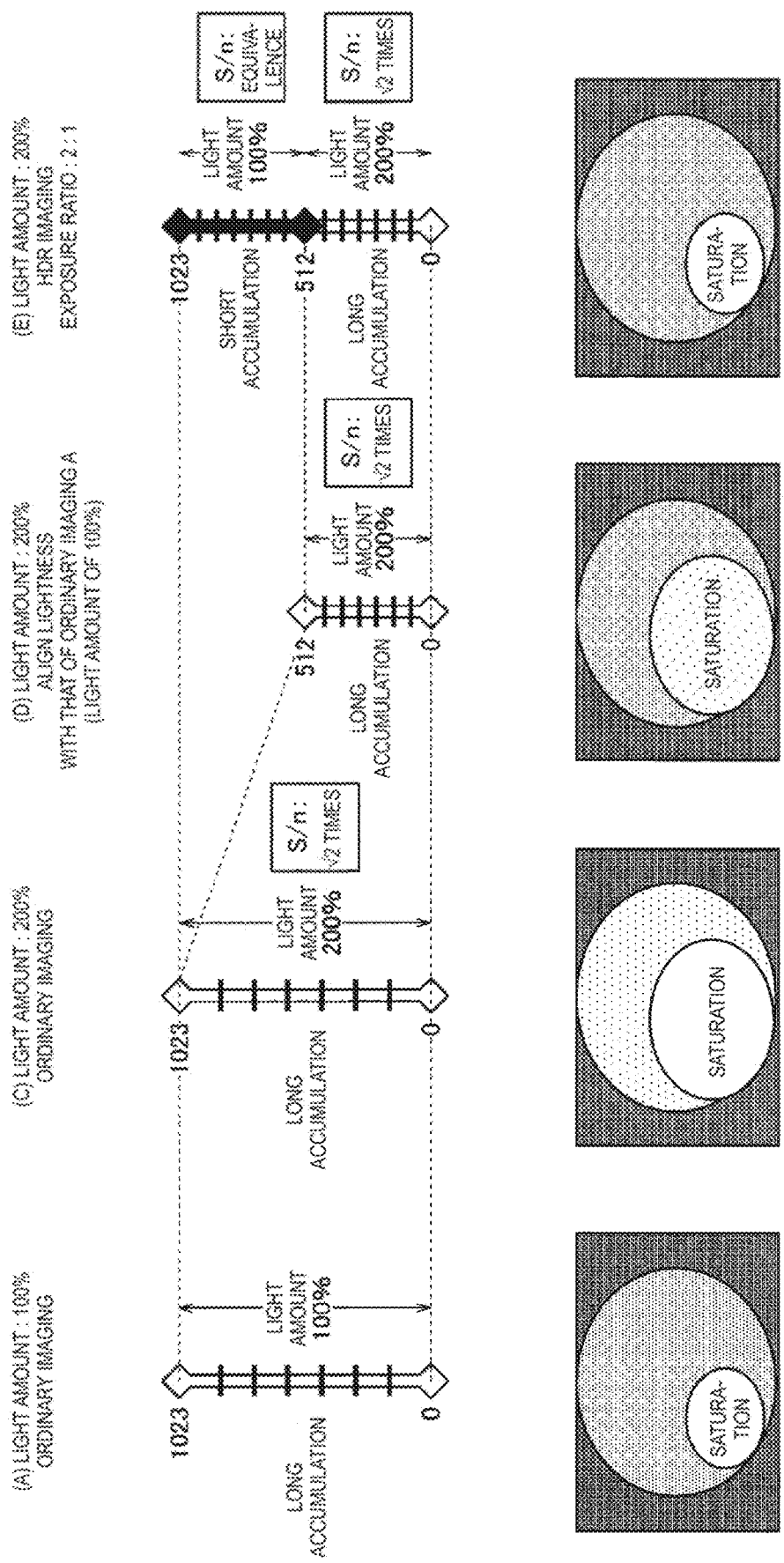
FIG. 5 is a schematic diagram showing a relationship among a light amount, s/n, and quantization accuracy.

FIG. 5 is a schematic diagram showing a relationship among a light amount, s/n, and quantization accuracy. In FIG. 5, the ordinary imaging (A) is similar to that shown in FIG. 4. The ordinary imaging (C) is that in which a light amount is made 200% relative to the ordinary imaging (A). In the ordinary imaging (C), since a amount becomes twice that in the ordinary imaging (A), the whole image becomes bright, and as shown in the lower stage in FIG. 5, a saturated region also increases. At this time, since the light amount becomes twice, s/n becomes √2 times.

In the ordinary imaging (D), the pixel value of the ordinary imaging (C) is made ½ correspondingly to a light amount (200%). With this, the lightness of an image is made aligned With that in the ordinary imaging (A) with a light amount of 100%. In this connection, the image processing section 100 performs adjustment of the pixel value. By aligning the lightness with that in the ordinary imaging (A) with a light amount of 100%, a pixel value larger than 512 is made not to exist. At this time, since it becomes to have 0 to 512 for 1023 gradations, the quantization accuracy becomes twice ordinary.

In the HDR imaging (E), for long accumulation pixels, it is made similar to that of the ordinary imagine (D), and, for short accumulation pixels, imaging is performed by making the light amount of an object 100%. With this, with respect to the long accumulation pixels, a dynamic range is 0 to 512. However, with respect to the short accumulation pixels, a dynamic range becomes 0 to 1023, so that the dynamic range is expanded than that in the ordinary imaging (D). The exposure ratio of the short accumulation pixels to the long accumulation pixels becomes 2:1. In the case where the HDR imaging, is performed with an exposure ratio of 2:1, a signal value (pixel value) larger than a pixel value of 512 also can be acquired. The overall lightness becomes similar to that of the ordinary imaging (A), and in the long accumulation pixels, relative to the ordinary imaging (A), s/n becomes √2 times, and quantization accuracy becomes twice. With this, although, the saturation level is the same as that in the ordinary imaging (A), s/n can be improved.

As shown in FIG. 5, by controlling an incident light amount to an image sensor, s/n and quantization accuracy can be improved. Here since sill has a characteristic of being proportional to the square root at a light amount, in the case where a light amount is made twice, s/n becomes √2 times.

Figure 6:
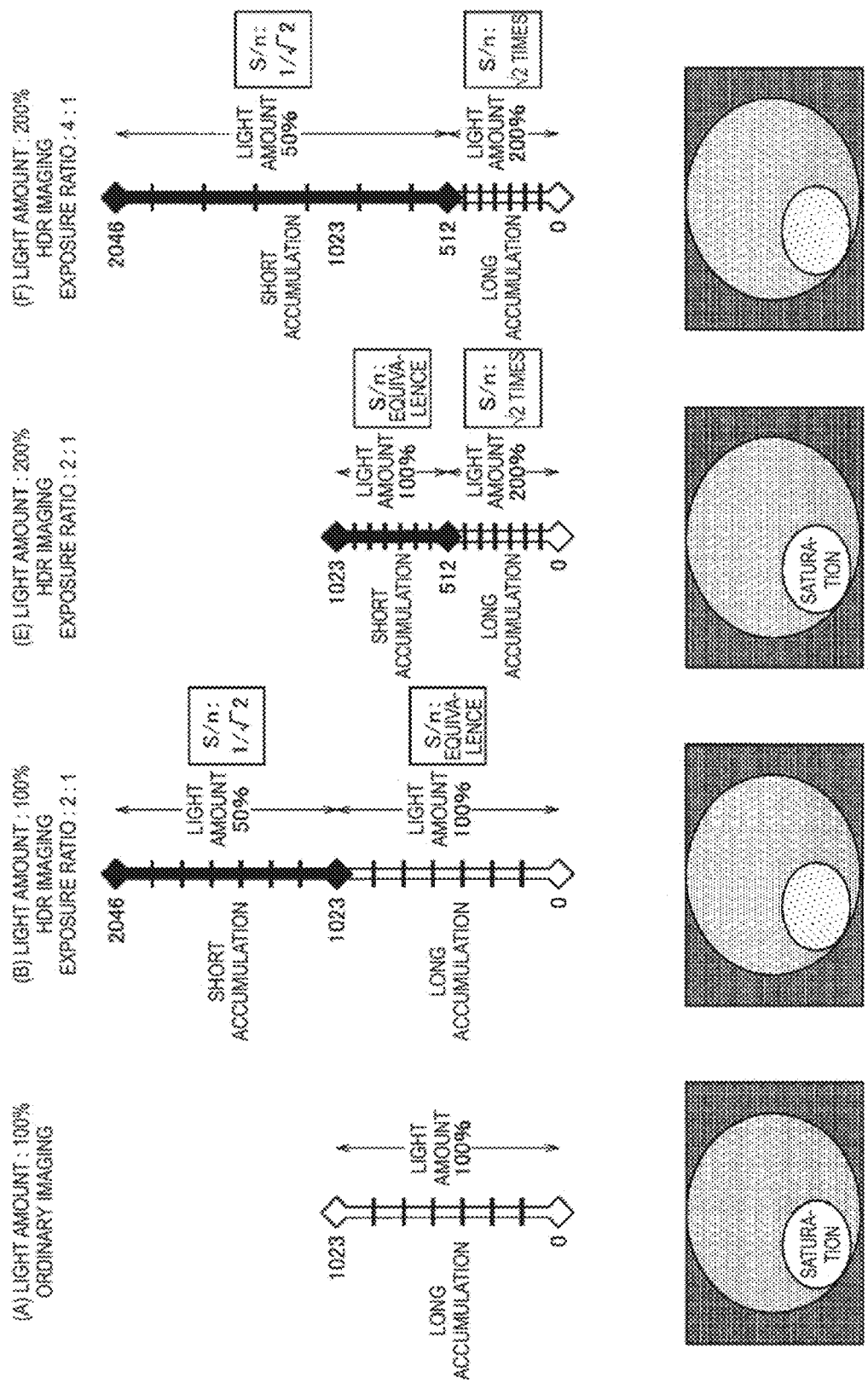
FIG. 6 is a schematic diagram showing a relationship among an exposure ratio, a light amount, and image quality.

FIG. 6 is a schematic diagram showing a relationship among an exposure ratio, a light amount, and an image quality. In FIG. 6, the ordinary imaging (A), the HDR imaging (B), and the HDR imaging (E) are similar to those shown in FIG. 4 and FIG. 5. In the HDR imaging (F), for long, accumulation pixels, it is made similar to that in the HDR imaging (E), and, for short accumulation pixels, imaging is performed by making the light amount of an object 50% and a pixel value acquired by the imaging is made twice. With this, with respect to the long accumulation pixels, a dynamic range is 0 to 512. However, with respect to the short accumulation pixels, a dynamic range becomes 0 to 2046, so that the dynamic range is expanded more. The exposure ratio of the short accumulation pixels to the long accumulation pixels becomes 4:1. Since the exposure ratio is 4:1, a saturation level is expanded by 4 times. However, since the light amount of the long accumulation pixels is 200%, in the case where a pixel value is made ½ (one half) in order to make the lightness the same as that at the time of a light amount of 100%, a substantial saturation level expansion becomes twice, in the short accumulation pixels, since a light amount is 50%, s/n becomes 1/√2 relative to the ordinary imaging (A).

Figure 7:
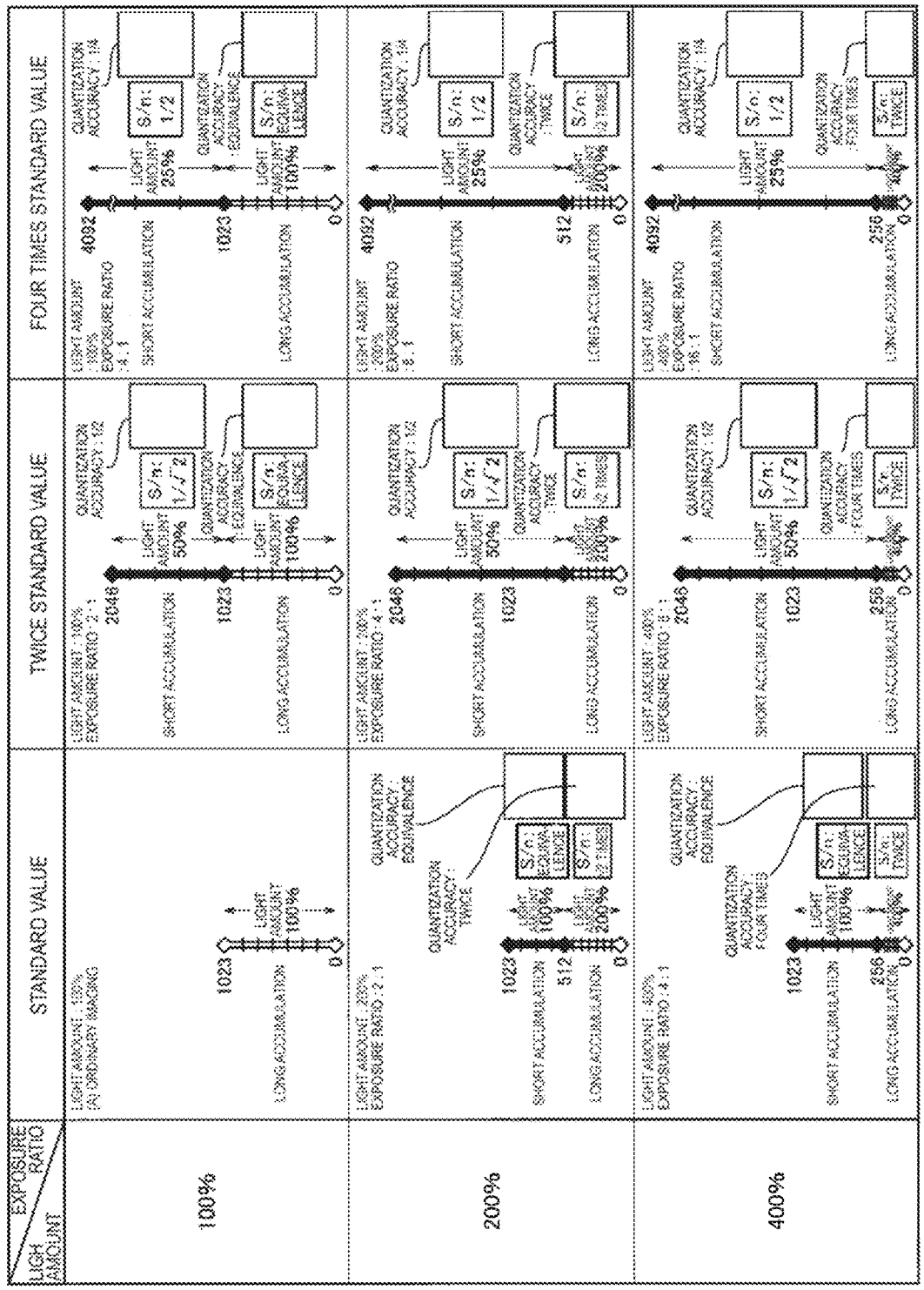
FIG. 7 is a schematic diagram showing an example of a combination of a light amount and an exposure ratio.

FIG. 7 is a schematic diagram showing an example of a combination of a light amount and an exposure ratio. As shown in FIG. 7, by combining a light amount and an exposure ratio optimally correspondingly to a photographing condition, a dynamic range can be secured optimally in this connection in FIG. 7, in the case where an exposure ratio is "the standard value", a dynamic range becomes 0 to 1023, in the case where the exposure ratio is "twice the standard value", the dynamic range becomes 0 to 2046, and in the case where the exposure ratio is "four times the standard value", a dynamic range becomes 0 to 4092. Accordingly, as an exposure ratio becomes larger than the standard value, the dynamic range is expanded. In FIG. 7, in concrete terms, on the basis of a light amount, the level band, s/n, and quantization accuracy of long accumulation pixels are determined. Moreover, the degree of expansion of a saturation level is determined by an exposure ratio. Moreover, the standard value of an exposure ratio is dependent on light amount setting. In the present embodiment, it is possible to acquire an optimal image by changing dynamically a light amount and an exposure ratio shown in FIG. 7 on the basis of image data obtained by imaging of the image sensor of the camera head 200. As mentioned above, in the case of having expanded the dynamic range of short accumulation pixels correspondingly to an exposure ratio, the image processing section 100 adjusts the pixel value of the short accumulation pixels correspondingly to an exposure ratio. For example, in the case where the light amount is 200% and the exposure ratio is 4:1, the pixel value of short accumulation pixels is made twice. Moreover, in the case where the light amount is 400% and the exposure ratio is 8:1, the pixel value of short accumulation pixels is made four times. With this, as shown in each example in FIG. 7, in the short accumulation pixels, a dynamic range can be expanded. Moreover, in the case of having increased the light amount of long accumulation pixels, the image processing section 100 adjusts the pixel values of long and short accumulation pixels correspondingly to the light amount. For example, in the case where the light amount is made 200%, the pixel value of the long accumulation pixels is made ½ (one half), and in the case where the light amount is made 400%, the pixel value of the long accumulation pixels is made ¼. In order to perform such adjustment of a pixel value, the light amount (%) and the exposure ratio are sent to the image processing section 100.

As shown in FIG. 6, although an apparent dynamic range is the same (the ordinary imaging (A) and the HDR imaging (E), the HDR imaging (B) and the HDR imaging (F)), it becomes possible to improve s/n and quantization accuracy in a lightness region equivalent to the long accumulation pixels. In the present embodiment, by setting an optimum combination of a light amount and an exposure ratio correspondingly to an image feature, it is made possible to output an image in which the expansion of a dynamic range, the improvement of s/n, and the improvement of quantization accuracy as shown in FIG. 7 have been attained.

4. With Regard to Light Amount Determining Process

Figure 8:
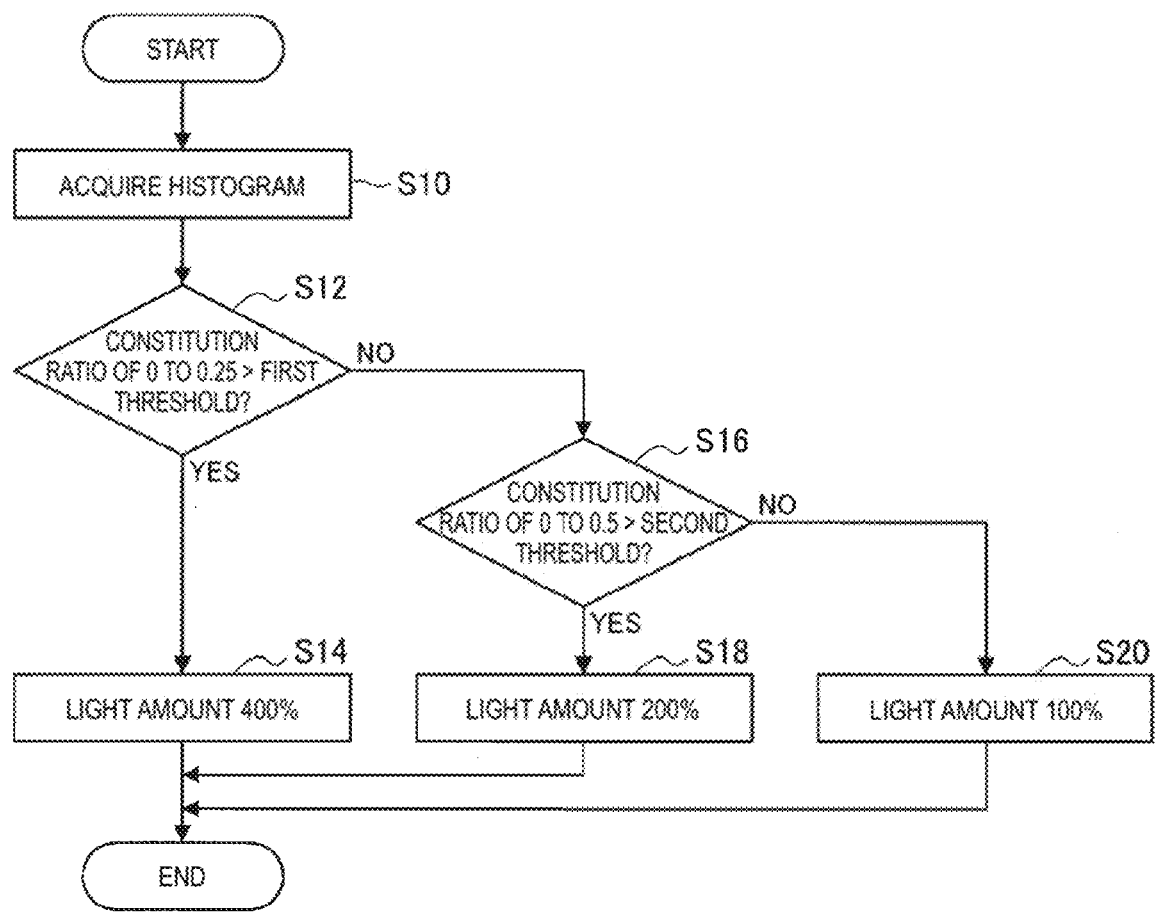
FIG. 8 is a flowchart showing a light amount determining process.

Next, a light amount determining process is described. FIG. 8 is a flowchart showing a light amount determining process. The determination of a light amount is performed by the light amount determining section 110 shown in FIG. 2. First, in Step S10, image data are acquired from the image sensor of the camera head 200, and a histogram showing the pixel value of each pixel is acquired, Moreover, in Step S10, pixel values of 0 to 1023 are normalized and converted into the values of 0 to 1.0. The values of 0 to 0.1 obtained by the conversion are ratios relative to the saturated pixel values of the image sensor.

In Step S10, signals to acquire a histogram may be any of Y, G, R, and B signals. Moreover, a region for which a histogram is acquired may be any, such as all pixels in a mask, an arbitrary region (a cutout region, etc. at the time of performing electronic zoom) in a mask, a tip region of a surgical tool, and a gazing region of a surgeon. Moreover, a light amount may not be limited up to 400%, but, may be more than it.

In the next Step S12, it is determined whether a ratio (constitution ratio) of the number of pixels with a converted pixel value of 0 to 0.25 to the number of whole pixels exceeds a first threshold, and in the case of exceeding, the first threshold, it proceeds to Step S14. In Step S14, the light amount is made 400%.

On the other hand, in Step S12, in the case where the constitution ratio does not exceed the first, threshold, it proceeds to Step S16. Then, it is determined whether a ratio (constitution ratio) of the number of pixels with a converted pixel value of 0 to 0.5 to the number of whole pixels exceeds a second threshold, and in the case of exceeding the second threshold, it proceeds to Step S18. In Step S18, a light amount is made 200%.

Moreover, in Step S16, in the case where the constitution ratio does not exceed the second threshold, it proceeds to Step S20, the light amount is made 100%.

As mentioned above, in the process in FIG. 8, in the case where the pixel values in a region of interest (a region for which a histogram is acquired) concentrate on low values, the process is performed such that the light amount is increased so as to improve the s/n of the pixel value band. As shown in FIG. 7, in the case where the light amount is made high, while s/n and quantization accuracy in a dark portion corresponding to the long accumulation pixels are improved as compared with the ordinary imaging (A), s/n and quantization accuracy in a light portion are the same as those in the ordinary imaging (A), or lower than those in the ordinary imaging (A). This is caused by a fact that the short accumulation pixels are utilized in the light portion. Therefore, in the case where there is almost no light portion within an image, since a light portion does not exist even if the light amount is made high, the lowering of s/n etc. is not visually confirmed. On the other hand, in an image in which a light portion occupies many, the lowering of s/n etc. is visually confirmed. In the light amount determining section, on the basis of the histogram of an image, the light amount is determined such that the lowering of an image quality becomes difficult to be visually confirmed.

The light amount determined by the process of FIG. 8 is sent to the light source device 6. The light source device 6 irradiates an object on the basis of the received light amount.

5. With Regard to Exposure Ratio Determining Process

Figure 9:
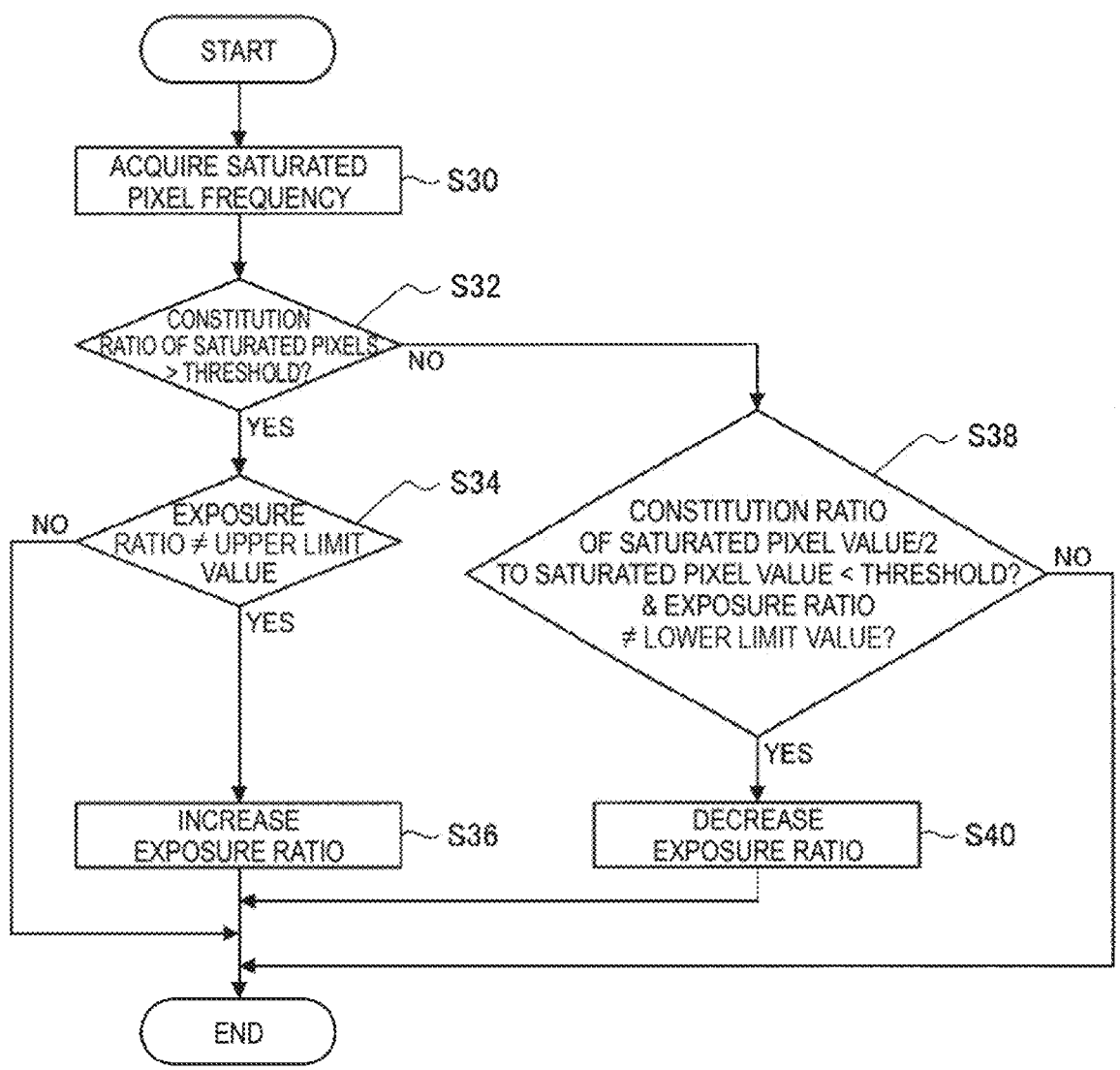
FIG. 9 is a flowchart showing an exposure ratio determining process.
Figure 10:
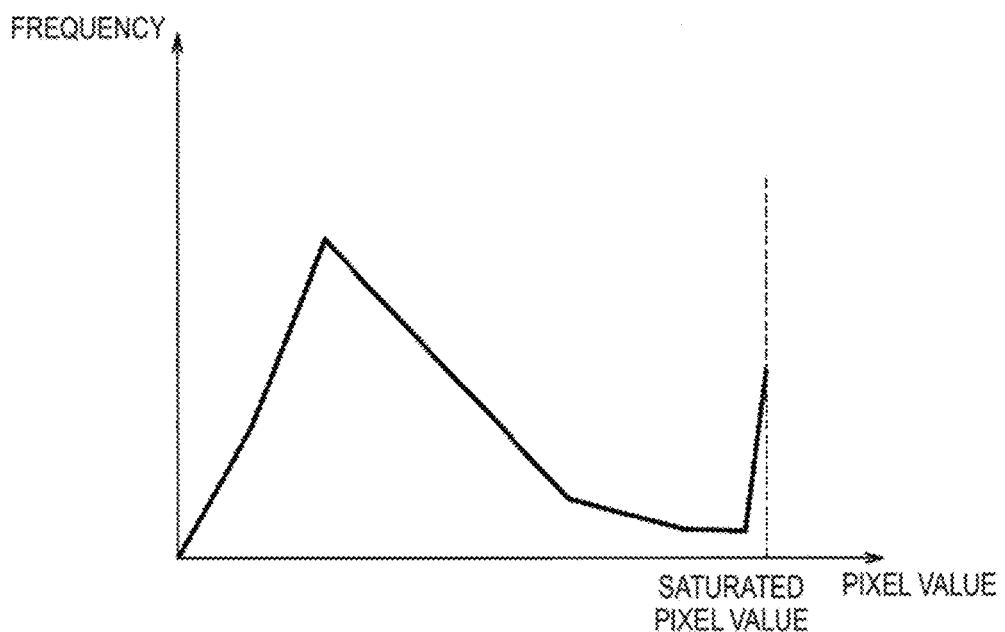
FIG. 10 is a schematic diagram showing the frequency of saturated pixels acquired at Step S30 of FIG. 9.
Figure 11:
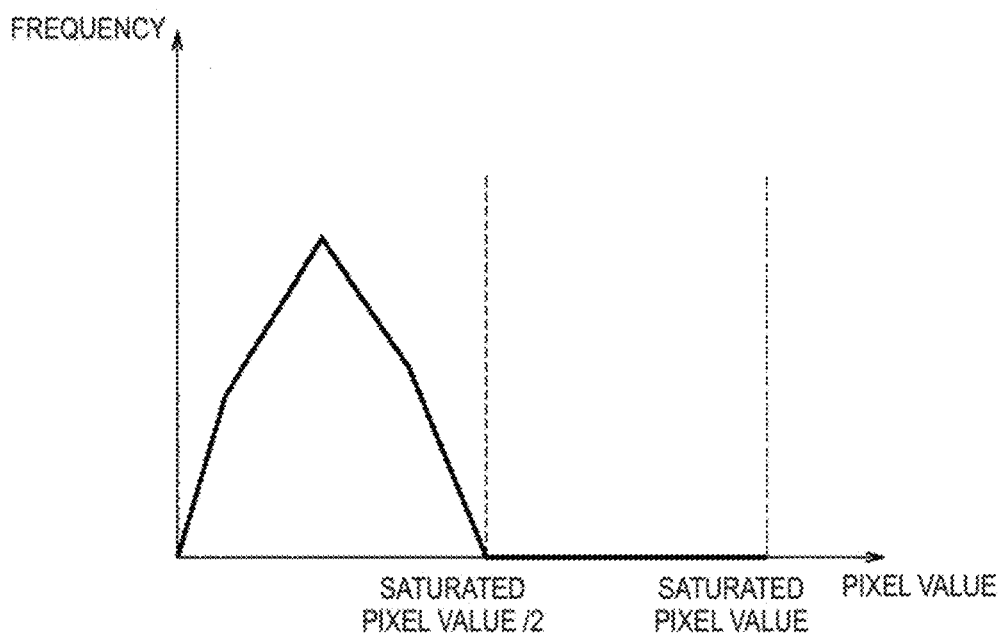
FIG. 11 is a schematic diagram showing the frequency of saturated pixels acquired at Step S30 of FIG. 9.

Next, an exposure ratio determining process is described. FIG. 9 is a flowchart showing an exposure ratio determining process. The determination of an exposure ratio is performed by the exposure ratio determining section 120 shown in FIG. 2. First, the frequency of saturated pixels is acquired in Step S30. As shown in FIG. 10 and FIG. 11, the frequency of saturated pixels is data that show the number of saturated pixels and the number of not saturated pixels by making pixel values the horizontal axis. In the next Step S32, it is determined whether the constitution ratio of saturated pixels exceeds the first threshold, and, in the case where the constitution ratio of saturated pixels exceeds the first threshold, it proceeds to Step S34, and it is determined whether the exposure ratio has coincided with the upper limit value. Then, in Step S34, in the case where the exposure ratio does not coincide with the upper limit value, it proceeds to Step S36, and the exposure ratio is increased. On the other hand, in Step S34, in the case where the exposure ratio coincides with the upper limit value, the process is ended.

Moreover, in the case where the constitution ratio of saturated pixels is a predetermined threshold or less in Step S32, it proceeds to Step S38, and it is determined whether a condition that the constitution ratio of pixels in a range of from ½ of the saturated pixel value to the saturated pixel value is less than the second threshold and a condition that the exposure ratio does not coincide with the lower limit value, are established together. Then, in the case where both conditions are established together, it proceeds to Step S40, and the exposure ratio is decreased.

In Step S36 and Step S40, the exposure ratio is increased or decreased only by a predetermined amount. In the case where the exposure ratio has reached the upper limit (Step S34), or in the case where the exposure ratio has reached the lower limit value (Step S40), the increasing or decreasing of the exposure ratio is not performed, and the exposure ratio is made the upper limit value or the lower limit value.

FIG. 10 and FIG. 11 are schematic diagrams showing the frequency of saturated pixels acquired in Step S30. In the histogram shown in FIG. 10, there are many saturated pixels, and the constitution ratio of saturated pixels becomes larger than the first threshold. Therefore, in the case of such an image, it proceeds from Step S32 to Step S36, and a process of increasing the exposure ratio is performed. Moreover, in the case where the exposure ratio has reached the upper limit value, the process is ended (Step S34).

Moreover, in the histogram shown in FIG. 11, the number of pixels in a range of from ½ of the saturated pixel value to the saturated pixel value is small. Therefore, in the case of such an image, it proceeds from Step S38, proceeds to Step S40, and a process of decreasing the exposure ratio is performed, in this, case, even if the exposure ratio is decreased, a large amount of saturated pixels do not occur. Moreover, in the case where the exposure ratio has reached the lower limit value (Step S38), the process is ended.

In this connection, in the process of FIG. 9, a saturated pixel is not a strictly-saturated pixel, and a pixel having a pixel value being a certain value or more may be made a saturated pixel. The lower limit value of the exposure ratio can be changed correspondingly to a light amount, and in the case where the light amount is 100%, it becomes 1, in the case where the light amount is 200%, it becomes 2, and in the case where the light amount is 400%, it becomes 4.

By the process of FIG. 9, in the case where there are many saturated pixels, the dynamic range is expanded by increasing the exposure ratio, and in the ease where there are few bright pixels including saturated pixels, since the dynamic range is unnecessarily expanded, the exposure ratio is decreased.

In this connection, a region referred at the light amount determining section 110 and the exposure ratio determining section 120 is made the entire region within a mask. However, a region referred at any of determining sections may be a region described below.

As mentioned above, by performing the processes of FIG. 8 and FIG. 9, the light amount and the exposure ratio can be set optimally on the basis of the imaged image. Therefore, while a desired dynamic range can be secured, it becomes possible to improve s/n.

5. With Regard to Mode Different from Present Embodiment

Figure 12:
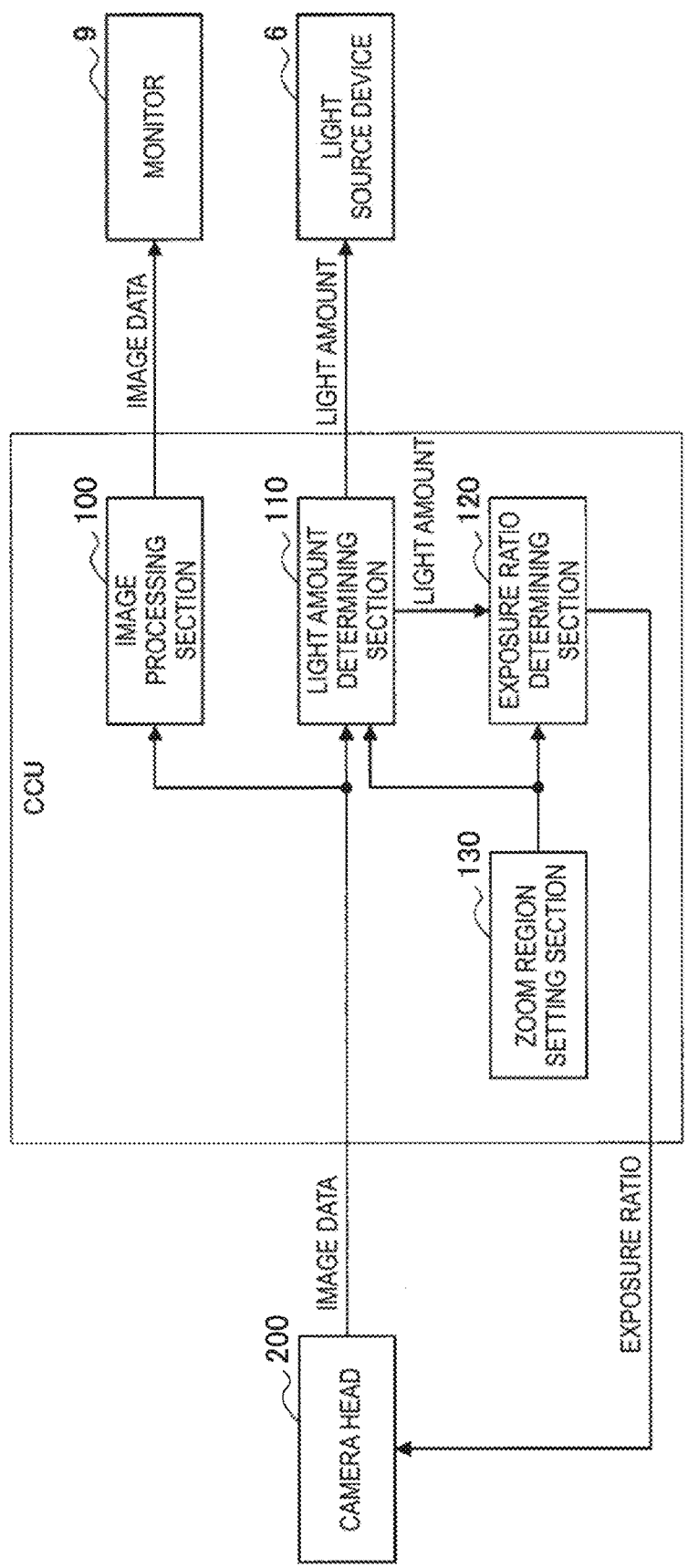
FIG. 12 shows an example in which a zoom region setting section is added to a constitution of FIG. 2.

Next, several different modes of the present embodiment will be described. FIG. 12 shows an example in which a zoom region setting section 130 is added to the constitution of FIG. 2. In the case, where an endoscope system includes an electronic zoom function, as shown in FIG. 12, the light amount determining section 110 and the exposure ratio determining section 120 acquire a zoom target region from the zoom region setting section 130. With this, although, in. FIG. 2, a region referred by the light amount determining section 110 and the exposure ratio determining section 120 is the entire region within a mask of an image, in FIG. 12, only a region (a cutout region of electronic zoom) actually displayed on the display device 9 is referred by the light amount determining section 110 and the exposure ratio determining section 120. Therefore, on the basis of a region displayed On the display device 9, it is possible to set a target region of acquisition of a histogram in the light amount determining section 110 and a target region of acquisition of a saturated pixel frequency in the exposure ratio determining section 120.

Figure 13:
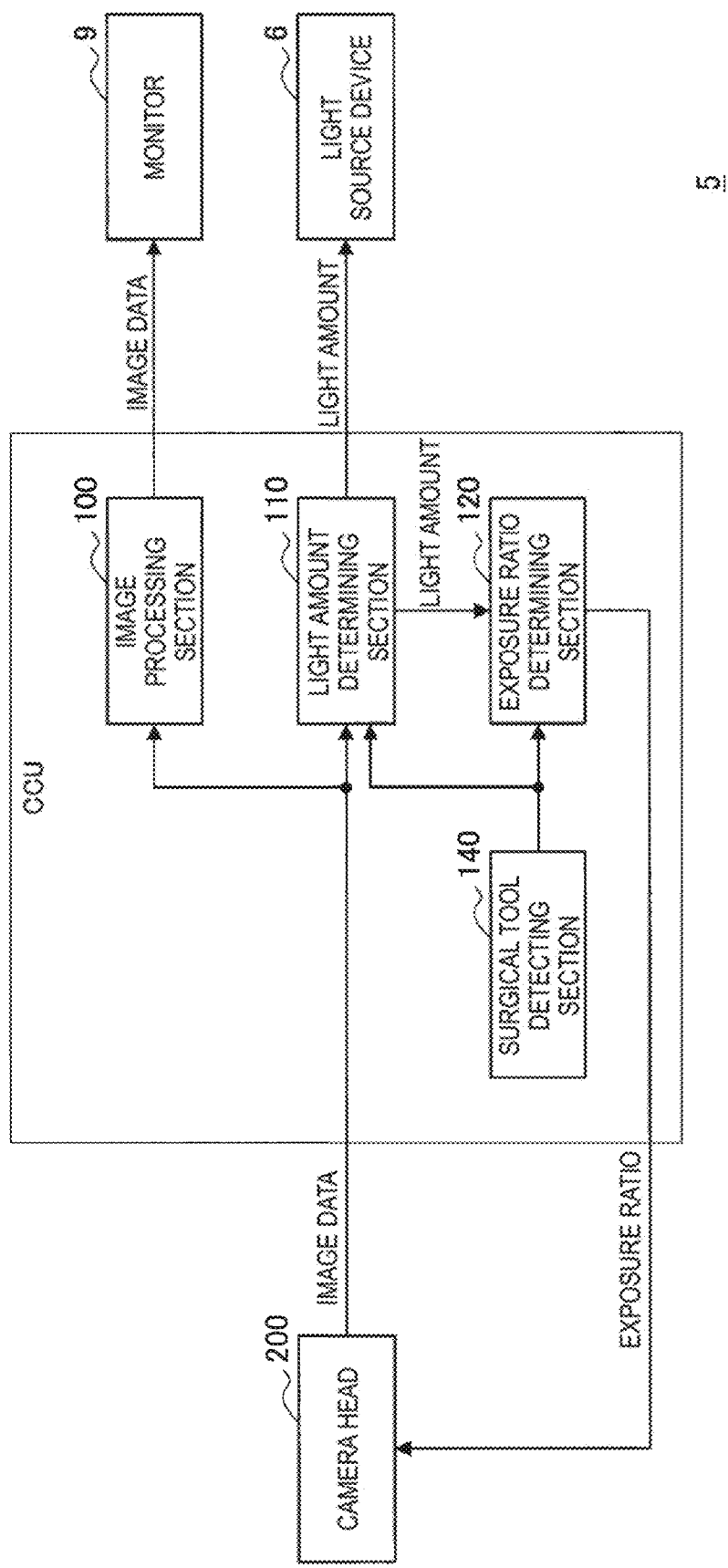
FIG. 13 shows an example in which a surgical tool detecting section 140 is added to a constitution of FIG. 2.

FIG. 13 shows an example in which a surgical tool detecting section 140 is added to the constitution of FIG. 2. By including the surgical tool detecting section 140, information indicating a tip region of a surgical tool is sent to the light amount determining section 110 and the exposure ratio determining section 120. With this, a region referred at the light amount determining section 110 or the exposure ratio determining section 120 is made a tip region (a region at which a tip of a surgical tool can arrive) of a surgical tool. Therefore, on the basis of the tip region of a surgical tool, it is possible to set a target region of acquisition of a histogram in the light amount determining section 110 and a target region of acquisition of a saturated pixel frequency in the exposure ratio determining section 120.

Figure 14:
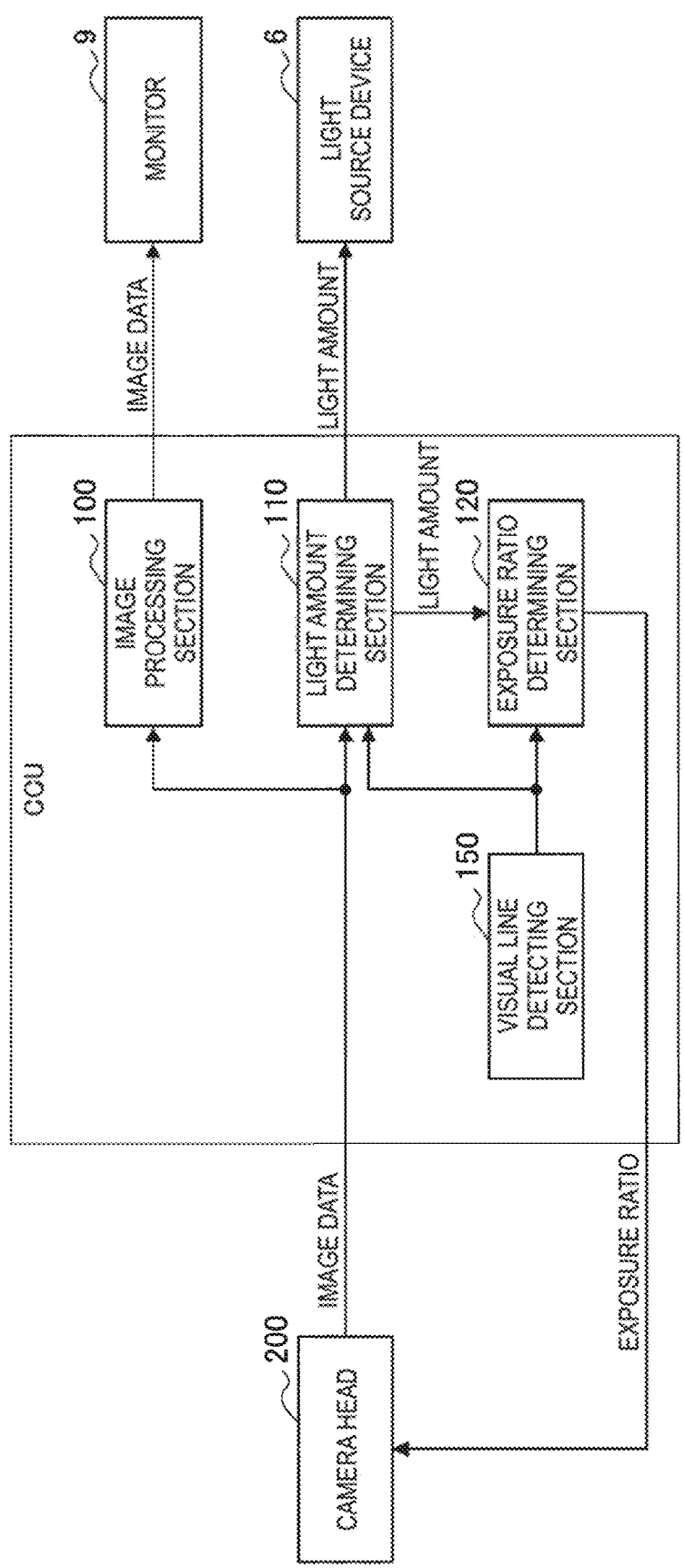
FIG. 14 shows an example in which a visual line detecting section 150 is added to a constitution of FIG. 2.

FIG. 14 shows an example in which a visual line detecting section 150 is added to the constitution of FIG. 2. By including the visual line detecting section 150, information indicating a region of a visual line of a surgeon is sent to the light amount determining section 110 and the exposure ratio determining section 120. With this, a region referred by the light amount determining section 110 or the exposure ratio determining section 120 is made a region of a visual line of a surgeon. Therefore, on the basis of a region of a visual line of a surgeon, it is possible to set a target region of acquisition of a histogram in the light amount determining section 110 and a target region of acquisition of a saturated pixel frequency in the exposure ratio determining section 120.

In this connection, a region to be referred may be not the same between the light amount determining section 110 and the exposure ratio determining section 120, in Step S10 in FIG. 8, a region for which the light amount determining section 110 acquires a histogram, may be any of all the pixels in a mask, an arbitrary region (a cutout region of electronic zoom) in a mask described in FIG. 12, a tip region of a surgical tool described in FIG. 13, and a gazing region of a surgeon described in FIG. 14. Similarly, in Step S30 of FIG. 9, a region for which the exposure ratio determining section 120 acquires a saturated pixel frequency, may be any of all the pixels in a mask, an arbitrary region (a cutout region of electronic zoom) in a mask described in FIG. 12, a tip region of a surgical tool described in FIG. 13, and a gazing region of a surgeon described in FIG. 14.

In the constitution described above, an incident light amount to an image sensor is restricted with a light amount irradiated from the light source device 6 to an object. However, an incident light amount to an image sensor may be adjusted by adjusting the F-value of the lens of the camera head 200 or an exposure time by the electronic shutter of the image sensor.

Figure 15:
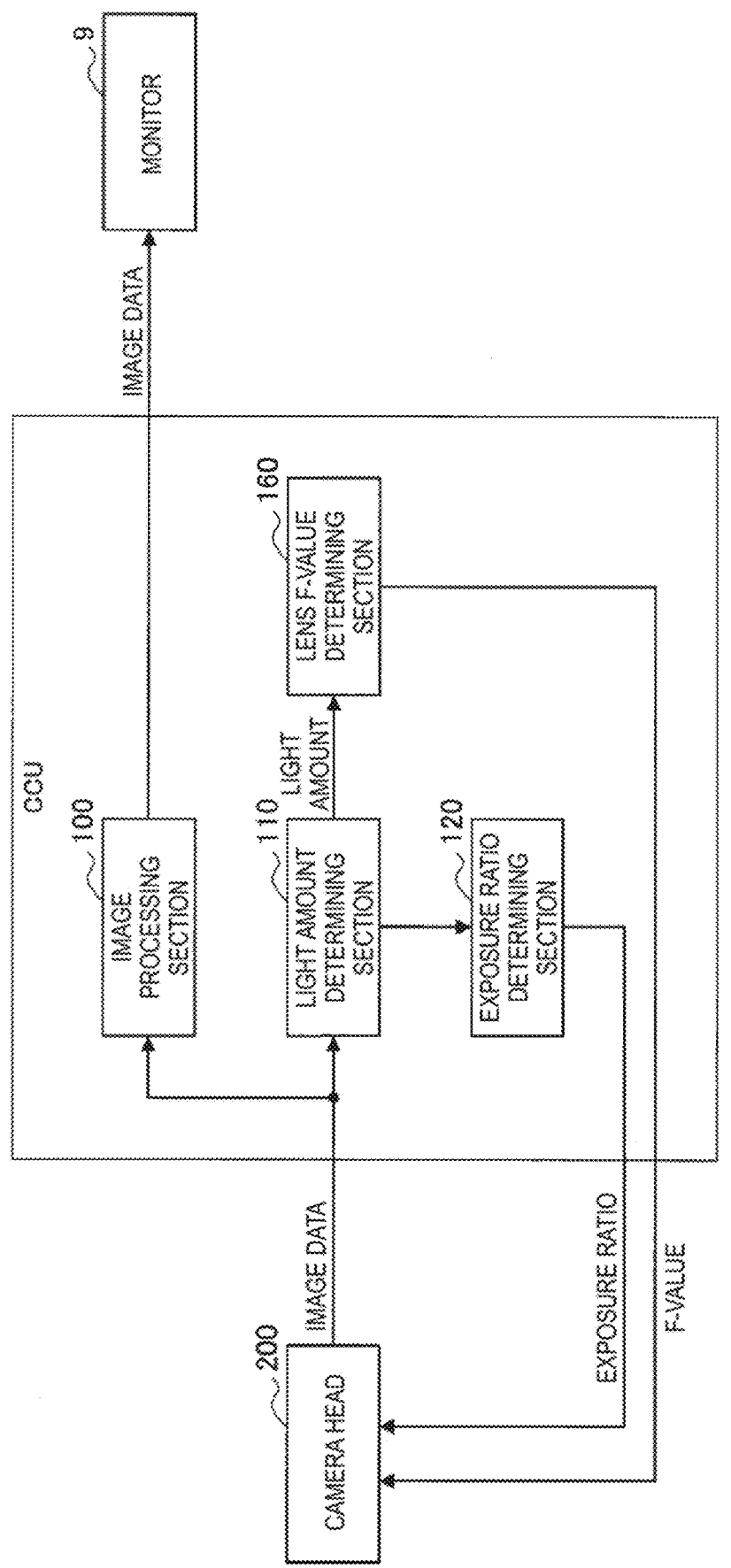
FIG. 15 is a schematic diagram showing an example in which an incident light amount to an image sensor is restricted by providing a diaphragm to a camera head.

FIG. 15 is a schematic diagram showing an example in which an incident light amount to an image sensor is restricted by providing a diaphragm to the camera head 200. In FIG. 15, a lens F-value determining section 160 is added to the constitution of FIG. 2 In the constitution shown in FIG. 15, since an incident light amount to an image sensor is restricted by a diaphragm, the light amount of an object can be adjusted with the diaphragm. For this reason, it is not necessary to provide the light source device 6.

In the constitution shown in FIG. 15, a light amount determined by the light amount determining section 110 is sent to the lens F-value determining section 160. The lens F-value determining section 160 determines the F-value of a lens correspondingly to a light amount on the basis of a table that describes the relationship between a light amount and the F-value of a lens or a transformation formula. The F-value is sent to the camera head 200. The camera head 200 drives the diaphragm on the basis of an F-value, and, restricts an incident light amount to an image sensor.

Figure 16:
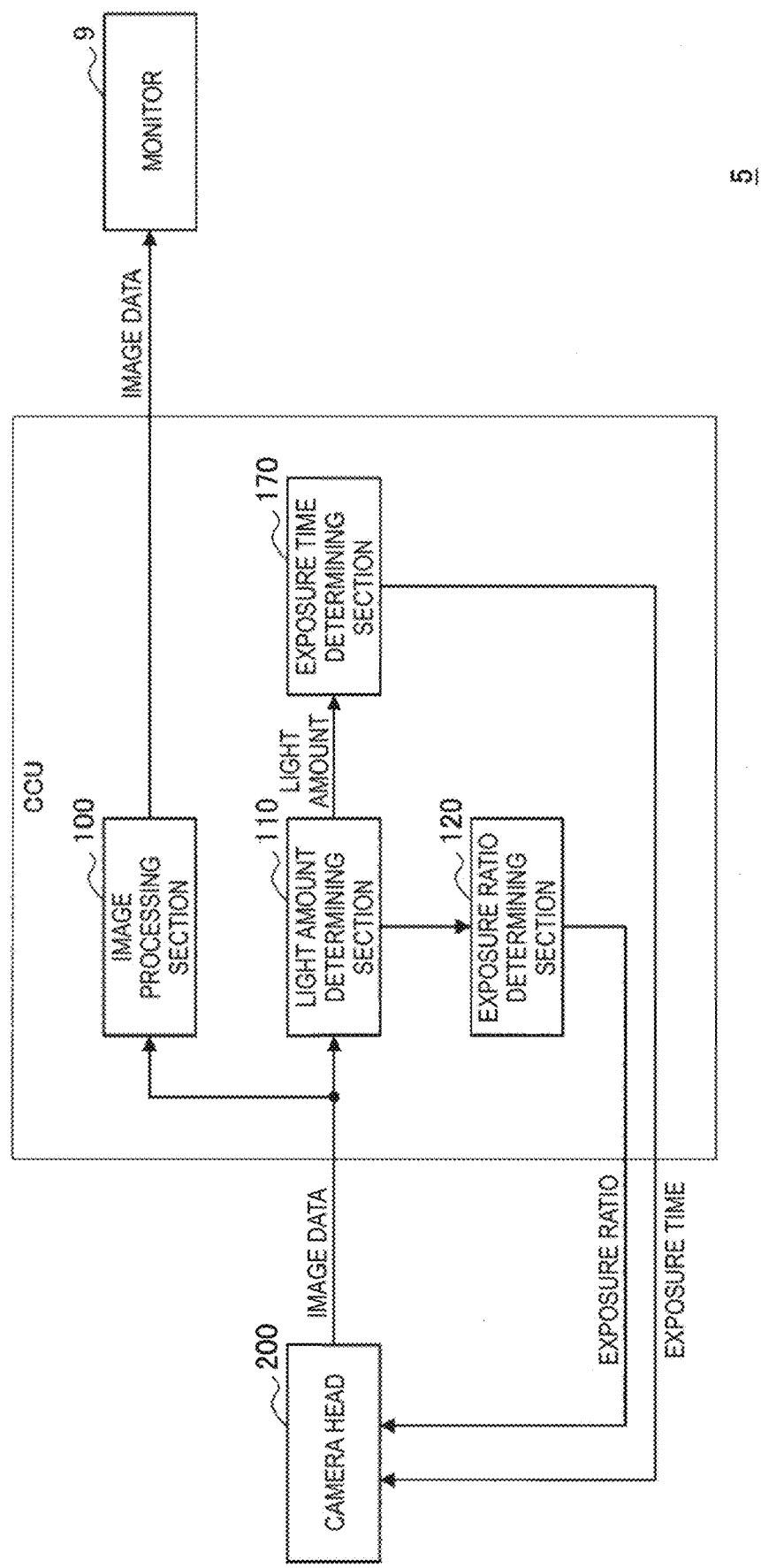
FIG. 16 is a schematic diagram showing an example in which an incident light amount to an image sensor is restricted by an exposure time.

FIG. 16 is a schematic diagram showing an example in which an incident light amount to an image sensor is restricted by an exposure time. In FIG. 16, an exposure time determining section 170 is added to the constitution of FIG. 2. In the constitution shown in FIG. 16, since an incident light amount to an image sensor is restricted by art exposure time, the light amount of an object can be adjusted with an exposure time. For this reason, it is not necessary to provide the light source device In the constitution shown in FIG. 16, a light amount determined by the light amount determining section 110 is sent to the exposure time determining section 170. The exposure time determining section 170 determines an exposure time correspondingly to a light amount on the basis of a table that describes the relationship between a light amount and an exposure time or a transformation formula. The exposure time is sent to the camera bead 200. The camera head 200 performs exposure with an, electronic shutter on the basis of the exposure time, and, restricts the incident light amount to an image sensor.

6. With Regard to Mixture of Long Accumulation Pixels and Short Accumulation Pixels Next, description is given for a process in which, after having acquired image data (pixel value) of long accumulation pixels and short accumulation pixels by doing as mentioned above, image data are generated by mixing (blending) long accumulation pixels and short accumulation pixels. As mentioned above, s/n becomes good by using long accumulation pixels. Accordingly, in the case where the lightness of an object is comparatively low and long accumulation pixels have not saturated, both pixels are mixed so as to make a ratio of long accumulation pixels large and to make a ratio of short accumulation pixels small. Therefore, the pixel value Po of an arbitrary pixel calculated from long accumulation pixels and short accumulation pixels can be represented by the following formula.

$$P_O = a*P_L + (1-a)*P_S$$

In the above formula, $P_L$ is the pixel value of the long accumulation pixel, $P_S$ is the pixel value of the short accumulation pixel, and, a coefficient "a" is a coefficient that changes correspondingly to the pixel value $P_L$ of the long accumulation pixel, and changes correspondingly to the pixel value $P_L$ of the long accumulation pixel. FIG. 17 is a characteristic diagram showing a situation that the value of the coefficient "a" changes correspondingly to the pixel value $P_L$ of the long accumulation pixel. In FIG. 17, the pixel value $P_L$ (for example 0 to 1023) of the long accumulation pixel is normalized, and, converted into a value of 0 to 1.0. Until the pixel value $P_L$ reaches the threshold $TH_L$, the coefficient "a" becomes one (1). Therefore, according to the above formula, the pixel value $P_O$ becomes the pixel value $P_L$ of the long accumulation pixel.

Moreover, in the case where the pixel value $P_L$ of the long accumulation pixel becomes larger than the threshold $TH_L$, as the pixel value $P_L$ becomes larger, the value of the coefficient "a" decreases. Furthermore, in the case where the pixel value $P_L$ reaches the threshold $TH_H$, the coefficient "a" becomes zero (0). Therefore, according to the above formula, the pixel value $P_O$ becomes the pixel value $P_S$ of the short accumulation pixel.

In this connection, as shown in FIG. 17, correspondingly to a method of mixing long accumulation pixels and short accumulation pixels, the value of the threshold $TH_L$ and the threshold $TH_H$ can be changed appropriately.

Figure 18:
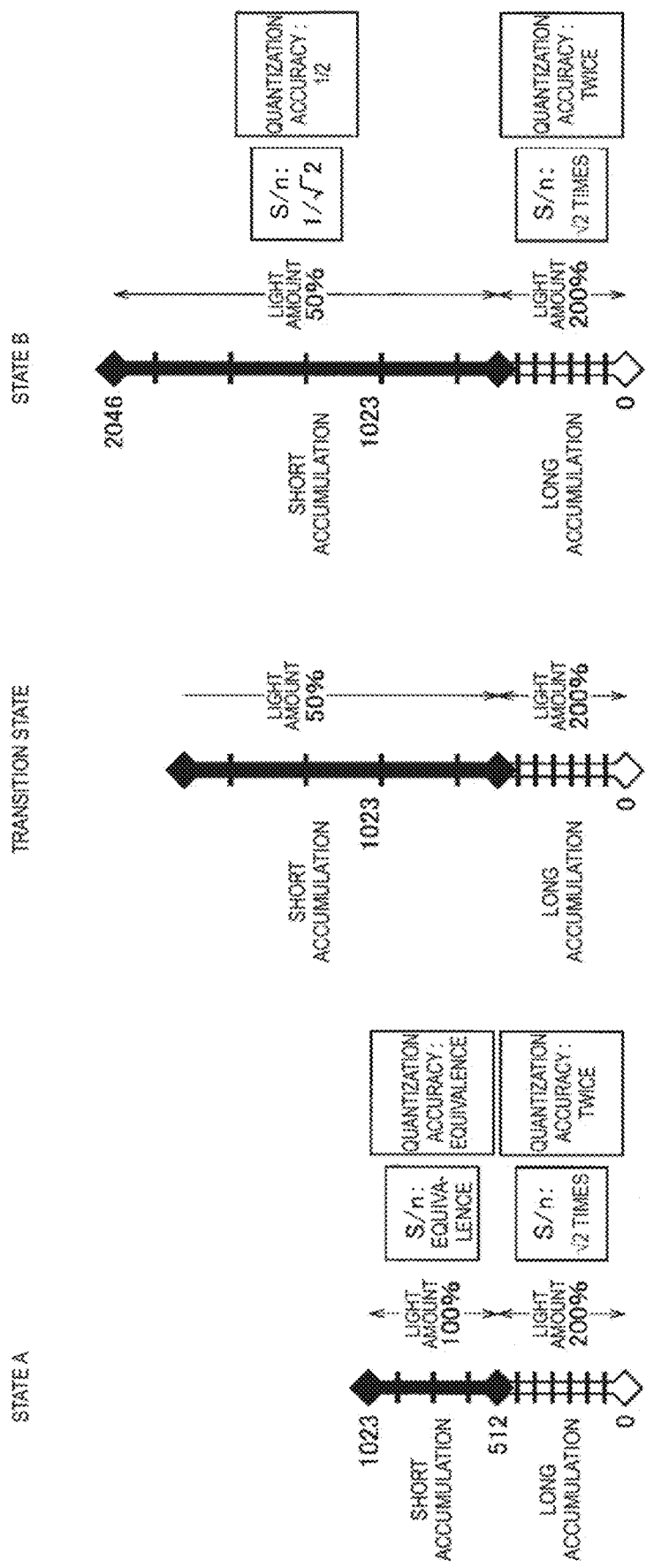
FIG. 18 is a schematic diagram showing an example in which a saturation level is changed in the case of transiting from a state A to a state B by changing a light amount and an exposure ratio.

Moreover, FIG. 18 is a schematic diagram showing an example in which a saturation level is changed at the time of transiting from a state A to a state B by changing a light amount and an exposure ratio, At the time of compressing gradation, the fluctuation of the maximum luminance is made gentle so that the fitness of a displayed image does not fluctuate rapidly: For example, at the moment of haying changed an exposure ratio, without changing the maximum luminance of short accumulation pixels from 1023 to 2046 in a moment, the maximum luminance is changed gradually so as to indicate a middle transition state. Moreover, an exposure time or a light amount of a light source on a short accumulation image side ma be changed gradually.

FIG. 19 is a schematic diagram showing an example in which a saturation level is not changed at the time of transiting from a state A to a state B by changing an exposure ratio. At the time of synthesizing an HDR image, the threshold of the blending is transited to a value matched with the state B such that regions in which short accumulation pixels and long accumulation pixels are mixed, become continuous. After having become a state of being coincident with the state B the light amount, the exposure ratio, etc. are changed to the state B. A light amount made to enter a long accumulation image sensor and a light amount made to enter a short accumulation image sensor may be made to change gradually.

7. Comparison Between Present Embodiment and Comparative Example

FIG. 20 is a schematic diagram showing by comparing the ordinary imaging (A), the HDR imaging (E) according to the present embodiment, and a comparative example (technique described in the above-mentioned Patent Literature 1) in the case of imaging the same object. Here, FIG. 20 shows a case of an object having no saturation. Hereinafter, differences between the present embodiment and the comparative example are described.

In FIG. 20, the luminance of each of three objects A, B, and C disposed at respective three staged depths is as shown in the ordinary imaging (A).

In the comparative example, in the case where the object A disposed far away is irradiated with a high light amount and in the case where the object B disposed nearer than it is irradiated with an ordinary light amount, if a light amount entering an imager is the same, s/n is not changed in the both cases. On the other hand, in the HDR imaging according to the present embodiment, s/n and quantization accuracy on the long accumulation pixel side are improved as mentioned above.

Moreover, in the comparative example, although the time division multi-stage exposure is performed, in the case where the time division multi-stage exposure is performed, the frame rate is decreased. In the present embodiment, in the case where the space division multi-stage exposure described in FIG. 3 has been performed, it is possible to suppress the decreasing of the frame rate.

Moreover, in the comparative example, since the average value of the pixel values is used, in the case where the frequency of each of low luminance and high luminance is many and the frequency of middle luminance is a few, it is determined as middle luminance as the average value. Moreover, in the comparative example, if saturated pixels are even one pixel, it may be pulled by it.

Moreover, in the comparative example, as shown in FIG. 20, a plurality of light source light amounts is controlled depending on a region. Accordingly, in the case where the boundary between a dark region and a light region does not coincide with the boundary of the light sources, the lightness of an object at the time of imaging becomes uneven. On the other hand, in the present embodiment, since a single light source is used, such a problem does not occur.

Moreover, in the comparative example, since the control of a light amount or an exposure ratio is performed by a feature amount within a region irradiated by a light source, if low luminance portions are a few in a target region, the appearance of the region cannot be improved. On the other hand, in the present embodiment, not only the whole screen, but also, by restricting a target region, such as a tip of a forceps and a gazing point of a user, it is possible to control a light amount or an exposure ratio from a feature amount in the region.

Furthermore, in the comparative example, since a low luminance region is irradiated brightly as compared with the other region, a dark region can be brightened up. However, it looks different from an original sense of contrast. On the other hand, in the present embodiment, persistently, at the time of imaging, the imaging is performed with an original sense of contrast, and it is possible to make a dark portion brighter by image processing (the degree of freedom in image creation is high).

Moreover, in the comparative example, there is no improvement in s/n and quantization accuracy on a low luminance portion of a region where a light amount is not increased. According to the present embodiment, it is also possible to improve s/n and quantization accuracy on all the low luminance portions within a screen.

As described above, according to the present embodiment, while expanding the dynamic range of an image, it is possible to improve s/n and quantization accuracy. At this time, by referring to the image feature of an object, it is possible to suppress the lowering of an image quality.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An image processing apparatus including:

a light amount determining section that determines, on a basis of a pixel value of each pixel of an imaged image, a light amount of the imaged image; and an exposure ratio determining section that determines a ratio of an exposure amount of a long time exposure pixel to an exposure amount of a short time exposure pixel on a basis of a ratio of pixels the pixel value of each of which is saturated, among pixels included in a region of the imaged image.

(2)

The image processing apparatus according to (1), further including:

an image processing section that adjusts a pixel value of each of the long time exposure pixel and the short time exposure pixel on a basis of the light amount and the ratio of the exposure amount.

(3)

The image processing apparatus according to (1) or (2), in which the light amount determining section determines the light amount on a basis of a ratio of pixels having a pixel value smaller than a predetermined pixel value among pixels included in the region of the imaged image.

(4)

The image processing apparatus according to (3), in which the exposure ratio determining section increases the ratio of the exposure amount in a case where the ratio is larger than a first threshold.

(5)

The image processing apparatus according to (4), in which in a case where the ratio is the first threshold or less, on a basis of at ratio of pixels having a pixel value from a predetermined pixel value to a saturated pixel value among pixels included in a region of the imaged image, in a case here the ratio is smaller than a second threshold, the exposure ratio determining section decreases the exposure ratio.

(6)

The image processing apparatus according to (5), in which the predetermined pixel value is ½ of the saturated pixel value.

(7)

The image processing apparatus according to any of (1) to (6), in which the region of the imaged image is determined correspondingly to zooming of a camera that images the imaged image.

(8)

The image processing apparatus according to any of (1) to (6), in which the region of the imaged image is determined correspondingly to a tip region of a surgical tool.

(9)

The image processing apparatus according to any of (1) to (6), in which the region of the imaged image is determined correspondingly to a region of a visual line of a surgeon.

(10)

The image processing apparatus according to any of (1) to (9), in which the light amount determining section sends the light amount to a light source that irradiates an object.

(11)

The image processing apparatus according to any of (1) to (10), in which in order to adjust an F-value of a camera that is the imaged image, the light amount determining section sends the light amount to the camera.

(12)

The image processing apparatus according to any of (1) to (11), in which in order to adjust an exposure time of a camera that images the imaged image, the light amount determining section sends the light amount to the camera.

(13)

The image processing apparatus according to any of (1) to (12), in which in order to make an image sensor that images the imaged image, adjust an exposure time of each of the lone time exposure pixel and the short time exposure pixel, the exposure ratio determining section sends the ratio of the exposure amount to a camera that images the images image.

(14)

The image processing apparatus according to any of (1) to (13), in which the lone time exposure pixel and the short time exposure pixel are disposed in a space of a same frame of the imaged image.

(15)

The image processing apparatus according to any of (1) to (13), which the long time exposure pixel and the short time exposure pixel are disposed on respective temporally-different frames of the imaged image.

(16)

The image processing apparatus according to any of (1) to (15), including:

an image processing section that performs a process of creating pixels in which the long time exposure pixel and the short time exposure pixel are mixed, in which the image processing section creates the mixed pixels in such a way that, on a basis of a pixel value of the long time exposure pixel, as the pixel value is smaller, a ratio of the long time exposure pixel to the short time exposure pixel is made larger.

(17)

An image processing method including:

determining, on a basis of a pixel value of each pixel of an imaged image, a light amount of the imaged image; and determining a ratio of an exposure amount of a long time exposure pixel to an exposure amount of a short time exposure pixel on a basis of a ratio of pixels the pixel value of each of which is saturated, among pixels included in a region of the imaged image.

(18)

A program for causing a computer function as:

means for determining, on a basis of a pixel value of each pixel of imaged image a light amount of the imaged image; and means for determining a ratio of an exposure amount of a long time exposure pixel to an exposure amount of a short time exposure pixel on a basis of a ratio of pixels the pixel value of each of which is saturated, among pixels included in a region of the imaged image.

REFERENCE SIGNS LIST

5 CCU
6 light source device
100 image processing section
110 light amount determining section
120 exposing ratio determining section
200 camera head

The invention claimed is:

1. An image processing apparatus, comprising:
processing circuitry configured to
determine, on a basis of a pixel value of each pixel of an image, a light amount of the image,
determine an exposure ratio of an exposure amount of a long time exposure pixel to an exposure amount of a short time exposure pixel on a basis of a ratio of saturated pixels to pixels included in a region of the image, and
adjust the exposure ratio when the ratio of the saturated pixels to the pixels included in the region of the image exceeds a first threshold and when the exposure ratio is not equal to a second threshold.

2. The image processing apparatus according to claim 1, wherein the processing circuitry is further configured to adjust a pixel value of the long time exposure pixel and a pixel value of the short time exposure pixel on a basis of the light amount and the exposure ratio.

3. The image processing apparatus according to claim 1, wherein the processing circuitry is further configured to determine the light amount on a basis of a ratio of pixels having a pixel value smaller than a predetermined pixel value to the pixels included in the region of the image.

4. The image processing apparatus according to claim 3, wherein the processing circuitry is further configured to increase the exposure ratio when the exposure ratio is not equal to the second threshold.

5. The image processing apparatus according to claim 1, wherein when the ratio of the saturated pixels to the pixels included in the region of the image does not exceed the first threshold, the exposure ratio is not equal to a third threshold, and a ratio of pixels having a pixel value from a predetermined pixel value to a saturated pixel value to the pixels included in the region of the image is lower than a fourth threshold, the processing circuitry is further configured to decrease the exposure ratio.

6. The image processing apparatus according to claim 5, wherein the predetermined pixel value is ½ of the saturated pixel value.

7. The image processing apparatus according to claim 1, wherein the region of the image corresponds to zooming of a camera that images the image.

8. The image processing apparatus according to claim 1, wherein the region of the image is a tip region of a surgical tool.

9. The image processing apparatus according to claim 1, wherein the region of the image is a region of a visual line of a surgeon.

10. The image processing apparatus according to claim 1, wherein the processing circuitry is further configured to send the light amount to a light source that irradiates an object.

11. The image processing apparatus according to claim 1, wherein in order to adjust an F-value of a camera that images the image, the processing circuitry is further configured to send the light amount to the camera.

12. The image processing apparatus according to claim 1, wherein in order to adjust an exposure time of a camera that images the image, the processing circuitry is further configured to send the light amount to the camera.

13. The image processing apparatus according to claim 1, wherein in order to adjust an exposure time of the long time exposure pixel and the short time exposure pixel, the processing circuitry is further configured to send the exposure ratio to a camera that images the image.

14. The image processing apparatus according to claim 1, wherein the long time exposure pixel and the short dine exposure pixel are disposed in a space of a same frame of the image.

15. The image processing apparatus according to claim 1, wherein the long time exposure pixel and the short time exposure pixel are disposed on respective temporally-different frames of the image.

16. The image processing apparatus according to claim 1, wherein the processing circuitry is further configured to create pixels in which the long time exposure pixel and the short time exposure pixel are mixed on a basis that a pixel value of the long time exposure pixel as the pixel value is smaller, so that a ratio of the long time exposure pixel to the short time exposure pixel is made larger.

17. The image processing apparatus according to claim 1, wherein the second threshold is an upper limit threshold.

18. An image processing method, comprising:
- determining, on a basis of a pixel value of each pixel of an image, a light amount of the image;
- determining an exposure ratio of an exposure amount of a long time exposure pixel to an exposure amount of a short time exposure pixel on a basis of a ratio of saturated pixels to pixels included in a region of the image; and
- adjusting the exposure ratio when the ratio of the saturated pixels to the pixels included in the region of the image exceeds a first threshold and when the exposure ratio is not equal to a second threshold.

19. A non-transitory computer-readable medium storing instructions which when executed by a computer cause the computer to perform a method, the method comprising:
- determining on a basis of a pixel value of each pixel of an image, a light amount of the image;
- determining an exposure ratio of an exposure amount of a long time exposure pixel to an exposure amount of a short time exposure pixel on a basis of a ratio of saturated pixels to pixels included in a region of the image; and
- adjusting the exposure ratio when the ratio of the saturated pixels to the pixels included in the region of the image exceeds a first threshold and when the exposure ratio is not equal to a second threshold.

* * * * *